US005576301A

United States Patent [19]

Hymer et al.

[11] Patent Number: 5,576,301
[45] Date of Patent: Nov. 19, 1996

[54] LOW MOLECULAR GROWTH POTENTIATING PEPTIDES

[75] Inventors: Wesley C. Hymer, Boalsburg; Krishnaswamy Krishnan, State College, both of Pa.; Wayne Lanham, Glen Carbon, Ill.

[73] Assignee: The Penn State Research Foundation, University Park, Pa.

[21] Appl. No.: 322,042

[22] Filed: Oct. 12, 1994

Related U.S. Application Data

[63] Continuation-in-part of Ser. No. 110,671, Aug. 23, 1993, abandoned, which is a continuation of Ser. No. 800,182, Nov. 27, 1991, abandoned.

[51] Int. Cl.$^6$ ............................. A61K 38/00; C07K 1/02
[52] U.S. Cl. ................................ 514/21; 514/12; 530/300
[58] Field of Search ........................ 514/12, 21; 530/300

[56] References Cited

U.S. PATENT DOCUMENTS 4,652,630  3/1987  Bentle et al. ............................ 530/344

OTHER PUBLICATIONS

Singh, R. M. P. et al. "Human Growth Hormone Peptide 1–43: Isolation from Pituitary Glands," J. Protein Chem. 2:6 (1983).

The Merck Index, 9th Edition, Martha Windholz, ed. issued 1976, p. 208.

Exhibit I–Dialog Search Report submitted with admendment files Dec. 21, 1995.

*Primary Examiner*—Elizabeth C. Weimar
*Assistant Examiner*—P. Lynn Touzeau
*Attorney, Agent, or Firm*—Thomas J. Monahan

[57]  ABSTRACT

Tibial growth potentiating peptides which are unreactive in an enzyme immunoassay for human growth hormone have been isolated from human pituitary glands and human plasma. The peptides have a molecular weight of less than 10,000 daltons.

15 Claims, 23 Drawing Sheets

LOW MOLECULAR GROWTH POTENTIATING PEPTIDES

GOVERNMENT SPONSORSHIP

This invention was made with Government support under Grants NAGW-1196 and NAG 8-953 awarded by the National Aeronautics and Space Administration. The Government has certain rights in the invention.

CROSS REFERENCE TO RELATED APPLICATIONS

This application is a continuation-in-part of Ser. No. 08/110,671 (abandoned), filed on Aug. 23, 1993, which is a continuation of Ser. No. 07/800,182, filed on Nov. 27, 1991 (abandoned). The entire contents of these two prior applications are incorporated by reference in their entirety.

FIELD OF THE INVENTION

The present invention relates to various growth potentiating proteins/peptides and their preparation and use.

DESCRIPTION OF RELATED ART

Over several decades, there have been reports concerning various forms of growth promoting substances contained in and released from the pituitary gland. These publications substantiate the presence of both bioactive and immunoreactive forms of human growth hormone (hGH) classically considered to be one of the major growth promoting substances. Currently, a recombinant form of hGH is used in the United States to treat patients. A major disadvantage of this material is that some patients (~20~30%) treated develop circulating antibodies, although these are presumed not to be harmful.

Clinical medicine uses only radioimmunoassay (RIA) to measure hGH in patients' serum. This method may miss alternative forms of proteins/peptides with high biological activity that may be in blood.

SUMMARY OF THE INVENTION

The present invention is directed to low molecular weight tibial growth potentiating peptides (TGPP) which have the following characteristics: potentiates tibial growth in hypophysectomized rats, a molecular weight of less than 10,000 daltons and is unreactive in an enzyme immunoassay for human growth hormone. These TGPP have been isolated from the human pituitary and human plasma by two different procedures.

These TGPP individually have a molecular weight of less than 5,000 daltons (when obtained from human pituitary) and less than 10,000 daltons (when obtained from human plasma).

Two peptides which have been isolated from the human pituitaries are designated HA-1 and HA-2; human adenohypophysis (HA). Peptide HA-1 has low activity in the tibial line assay relative to that of HA-2. Both peptides are unreactive in an enzyme immunoassay for hGH.

Nine peptides have been isolated from cryo-poor human plasma. Peptides isolated from human plasma (HPL) with significant tibial growth potentiating activity are designated HPL-1, HPL-3 and HPL-7; whereas peptides with lower activity are designated HPL-2, HPL-4, HPL-5, HPL-6, HPL-8 and HPL-9. Initial amino acid sequence determination of a sample containing both HA-1 and HA-2 indicates that the peptide has 25 or more residues with residues 9–25 being set forth in SEQ. ID. NO. 2, and appears as a single band on isoelectric focusing gels with a pI of about 5.1. The molecular weight of growth potentiating peptides HA-1 and HA-2, assessed by mass spectrometry, indicates they have molecular weights in the range of 3374–4314. Amino acid composition analysis of these peptides reveals that they are acidic in nature.

The present invention is also directed to a pharmaceutical composition for stimulating growth in a patient which comprises the above-described peptide and a pharmaceutically acceptable carrier therefor.

The present invention is also directed to a method for stimulating growth in a patient, especially a child, which comprises administering the above-described peptide to the patient.

DETAILED DESCRIPTION OF THE INVENTION

Figure 1:
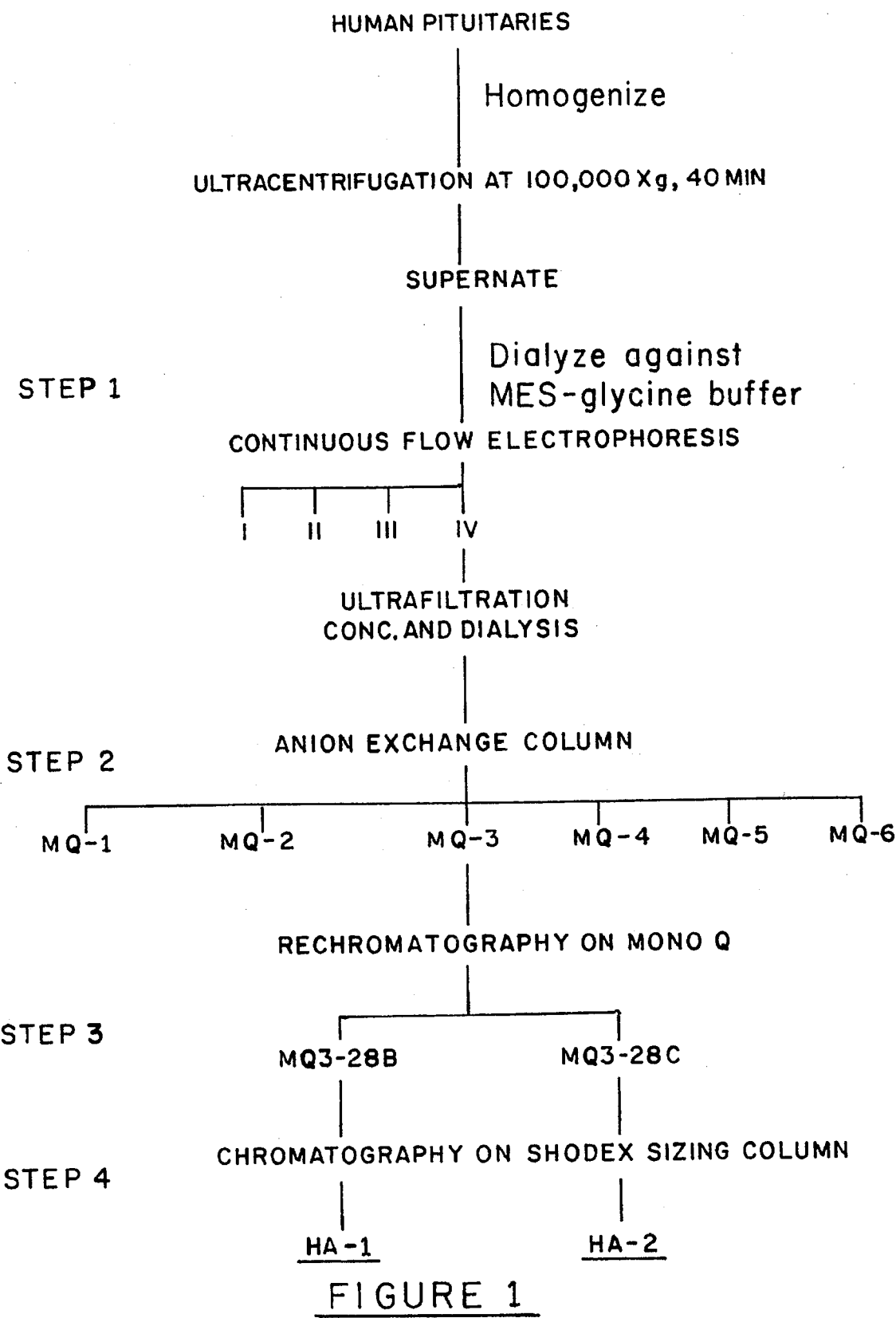
FIG. 1 is a schematic outline which summarizes the procedure used for isolation of HA-1 and HA-2 from human post-mortem pituitaries.

After the peptide has been suitably purified, the peptide will usually be mixed with a pharmaceutically acceptable carrier prior to administration. Various types of pharmaceutically acceptable carriers which are known in the art can be used. Pharmaceutically acceptable carriers which are especially designed for use with proteins and peptides are preferably employed. The pharmaceutically acceptable carrier should be sterile, non-toxic and free of any materials which are not necessary to provide a suitable environment for storage or administration of the peptide. The peptide is preferably stored in a dried state in a sterile container. Prior to administration, a physiological buffer such as physiological saline or phosphate buffered saline is mixed with the powder to prepare a suspension, solution or emulsion of the peptide for administration to the patient.

The peptide can be administered to a human patient by routes of administration and at dosages which are known in the art for natural human growth or recombinant human growth hormone. It is expected that the peptide of the present invention may be useful for treatment of conditions which can be treated by human growth hormone. These conditions include actions on different tissues that are (1) either stimulatory in character; namely on liver, muscle, bone, cartilage, kidney and skin or (2) inhibitory; namely the breakdown of fat (Corpas, E., et al., 1993. *Endocrine Reviews* 14(1):20–39). These actions are also sometimes classified as either physiologic, metabolic or anatomic (Chawla, R. K., et al. 1983. *Annu. Rev. Med.* 34). Dual effects of growth hormone on carbohydrate, either as an insulin agonist or insulin antagonist, have been known for some time (Davidson, M. B., 1987. *Endocrine Reviews*, Vol. 8(2):115–131). Finally, growth hormone probably plays a role in regulating activities of cells of the immune system. For example, Kelley, K. W., 1989. *Biochemical Pharmacology*, Vol. 38(5):705–713 has claimed " . . . in the future, growth hormone may be used clinically for a wide variety of other (basides promoting growth) applications, such as aiding wound healing, repartitioning fat into muscle, reversing certain aspects of aging and immunopotentiation in conjunction with vaccines (pg. 710)".

EXAMPLE 1

Isolation from Human Pituitary Glands
Extraction

Frozen human pituitary glands were obtained over dry ice from National Disease Research Interchange (NDRI). A total of six batches of two to ten pituitary glands/batch were utilized in these studies. The frozen pituitaries were thawed, cleaned to remove extraneous tissues, chopped into small pieces in a plastic petri dish, and transferred to a 50 ml polycarbonate tube containing 30 ml of 0.05M sodium bicarbonate buffer, pH 10, and 1 mM 4-aminobenzamidine dihydrochloride (protease inhibitor). The tissue was disrupted using a homogenizer (Biohomogenizer, Biospec Products, Bartlesville, Okla.) three times for 30 seconds each and the tissue extract then diluted to 100 ml in the same buffer (20 ml/pituitary). Extraction continued overnight at 4° C. with constant shaking. The homogenate was then centrifuged at 100,000×g for 40 minutes, and the 100,000×g supernatant was dialyzed overnight (14,000 MW cut-off) against continuous flow electrophoresis (CFES) buffer, pH 6.0 (3 mM MES (2-{N-Morpholino}ethanesulfonic acid), 0.2M glycine, 0.12M glycerol). The dialyzed material (dialysate) was used for purification of the growth potentiating peptides. This material was tested for the presence of C-JD virus by Dr. C. J. Gibbs, Jr, at the NIH and all samples were negative.

Purification

All operations except HPLC were performed at 4° C. unless otherwise noted. HPLC was performed at laboratory ambient temperatures (about 22° C.) on Waters HPLC 600 E system (Waters, Milford, Mass.).

Step 1

Figure 2A:
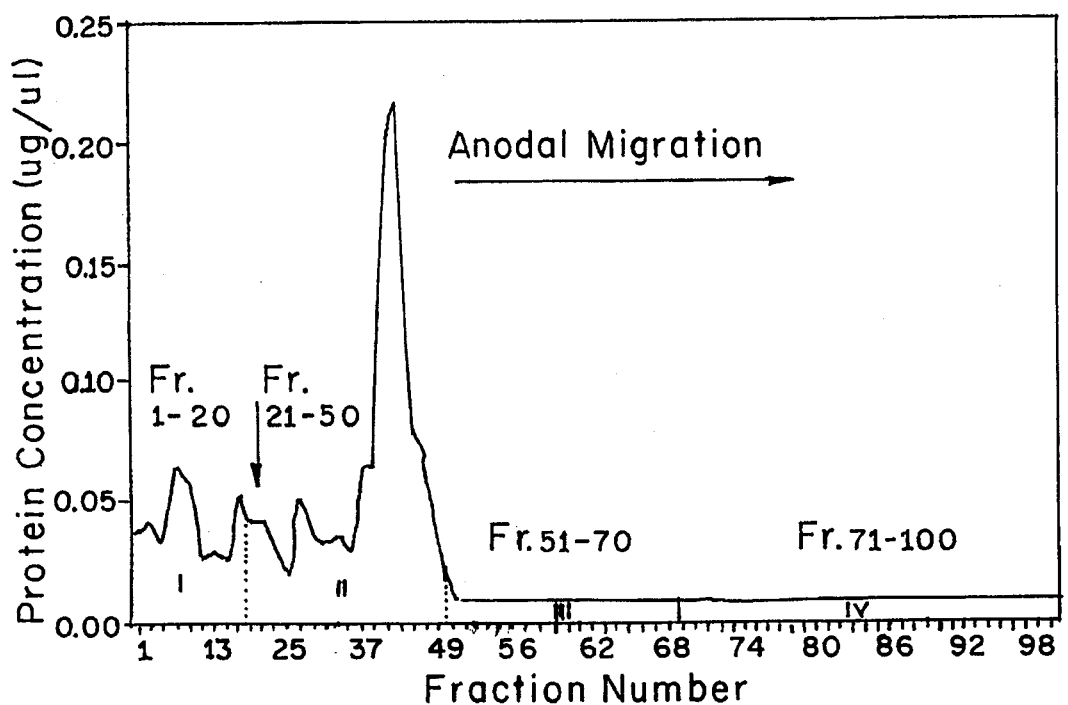
FIGS. 2A and 2B are graphs which show protein and absorbance elution profiles, respectively, of human pituitary dialysate after continuous flow electrophoresis (CFES)
Figure 2B:
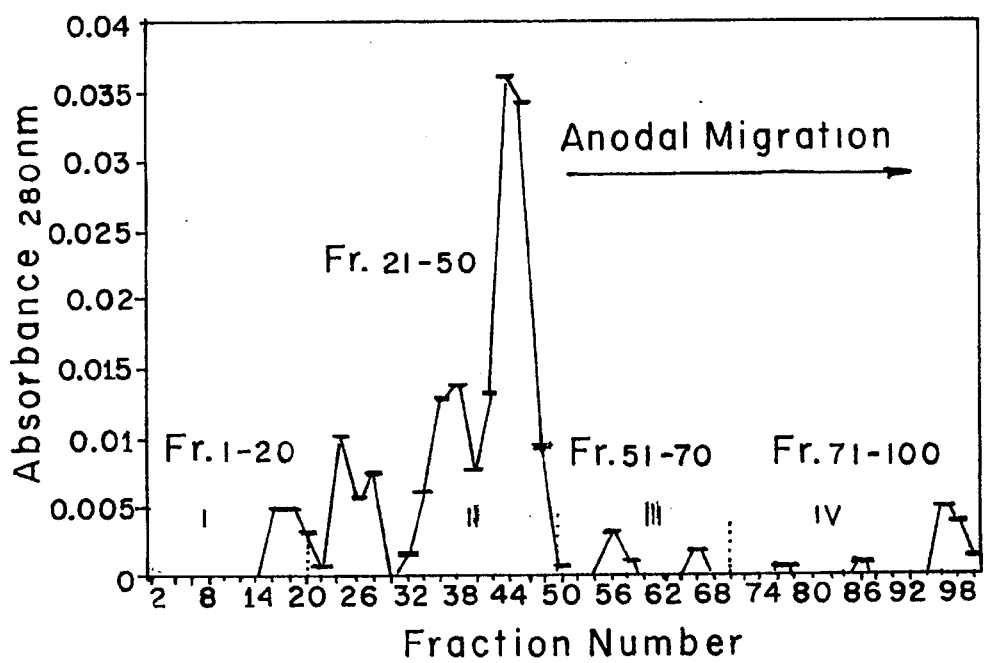

Continuous flow electrophoresis (CFES)—The dialysate was applied to the CFES unit, a device built by McDonnell-Douglas Corporation (St. Louis, Mo.) which has been described previously, Plank, et al., *J. Biochem. Biophys. Methods*, 8, 275–289 (1983) and Hymer, et al., *Cell Biophysics*, 10, 61–85 (1987). The CFES unit consists of a rectangular separation chamber 120 cm high, 8.2 cm wide, and 1.8 mm in depth and is sandwiched between two electrode chambers, which also serve as a cooling jacket. The electrode chambers are separated from the separation chamber at its edges by semipermeable membranes. A stable electrical field is maintained by ion flow through the membranes. Operating conditions for these experiments were: 24.7 v/cm, 12 ml/fraction/hr; 4°–6° C. Molecules in the sample flow upward and out through one of the 100 exit ports into individual collection tubes. Fractions were pooled as follows: FR-I (1–20), FR-II (21–50), FR-III (51–70), and FR-IV (71–100) (FIGS. 2A, 2B).

Ultrafiltration

Figure 3A:
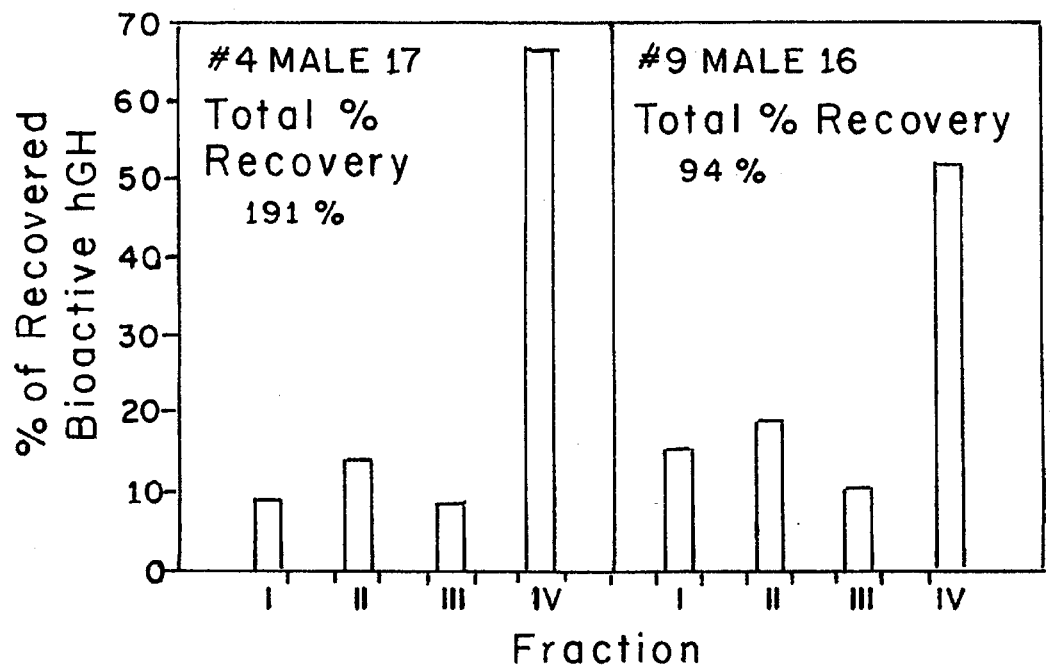
FIGS. 3A and 3B show the distribution of bioassayable growth potentiating activity (FIG. 3A) and immunoreactivity (FIG. 3B) of human pituitary dialysate after continuous flow electrophoresis.
Figure 3B:
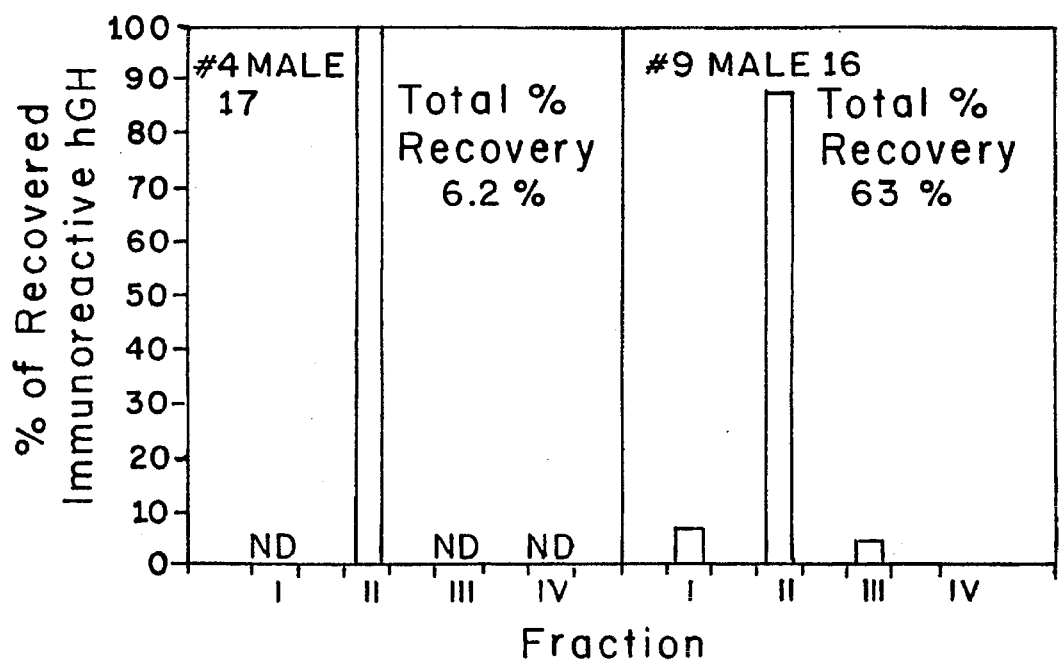

CFES fractions were concentrated on Amicon RA2000 (model CH2PRS, Amicon, Beverly, Mass.) fitted with a spiral-wound membrane cartridge (1000 MWCO), followed by dialysis on an Amicon ultrafiltration cell fitted with YM-1 membrane (1000 MWCO), and tested for growth potentiating activity by tibial line bioassay (FIGS. 3A, 3B).

Step 2

Figure 7:
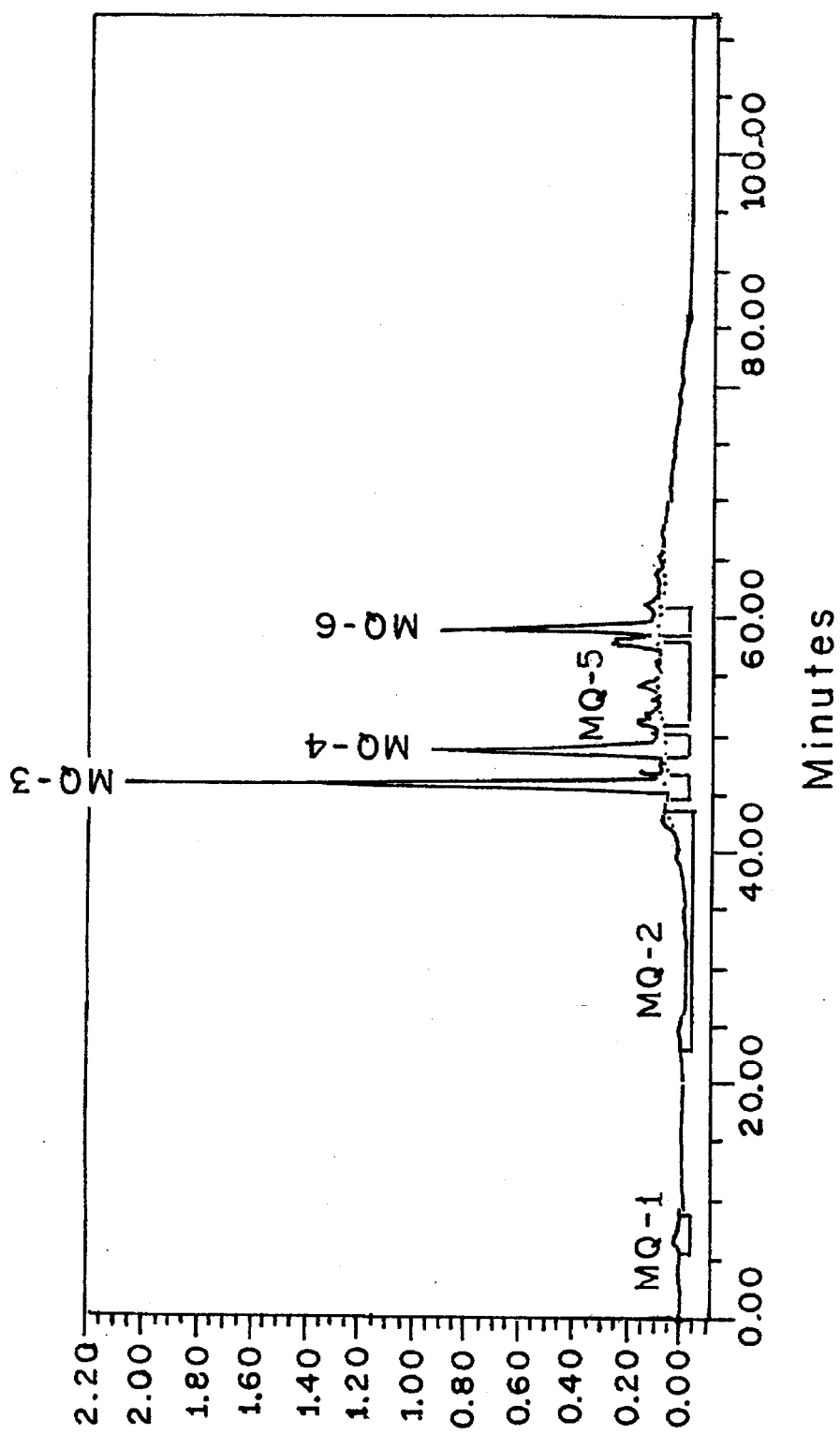
FIG. 7 is an elution profile of the concentrated continuous flow electrophoresis anodal fraction IV on an anion exchange column (Mono Q), fractions were pooled as indicated.

Anion exchange chromatography: The pooled, lyophilized peptide FR-IV (71–100) from Step 1 was reconstituted in 20 mM Tris-HCl buffer, pH 8.0, and applied to an anion exchange column (Mono Q, HR 10/10 column; Pharmacia-LKB Biotechnology) equilibrated with 20 mM Tris-HCl, pH 8.0 (FIG. 7). Unbound sample was eluted with the equilibration buffer ( 20 mM Tris-HCl, pH 8.0 ) at a flow rate of 1 ml/min for 20 min. Bound proteins were eluted at the same flow rate with a 50 minute linear gradient from zero to 100% equilibration buffer containing 0.6M sodium chloride, then 100% buffer containing 0.6M sodium chloride, followed by a 22 min re-equilibration prior to the next run. Protein content was monitored throughout the purification by measuring the absorbance at 280 nm. Fractions were pooled as follows: MQ-1 (fr. 3–6), MQ-2 (fr. 15–29), MQ-3 (fr. 30,31), MQ-4 (fr. 32,33), MQ-5 (fr. 34–38), and MQ-6 (fr. 39,40). These were concentrated, dialyzed on an Amicon cell fitted with a YM-1 membrane (1000 MWCO), and tested for growth potentiating activity by tibial line bioassay. The active fractions from 5–6 runs were pooled, concentrated on an Amicon cell fitted with a YM-1 membrane, dialyzed against 0.001M ammonium bicarbonate buffer, and lyophilized.

Step 3

Figure 9:
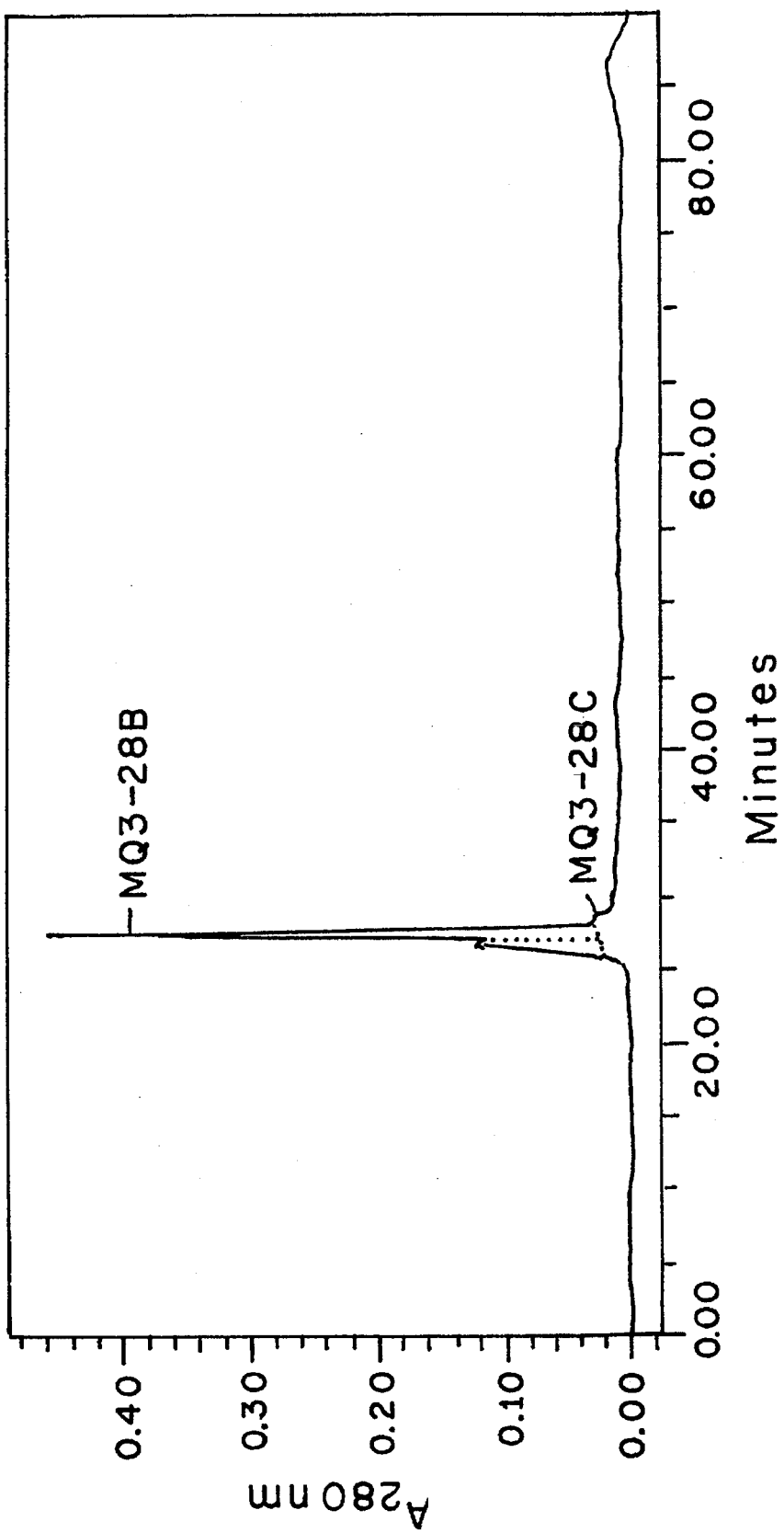
FIG. 9 is the elution profile of fraction MQ-3 after rechromatography on a Mono Q anion exchange column.

Re-chromatography on Mono Q—The pooled, lyophilized, bioactive peptide fraction (MQ-3) from Step 2 that contained the tibial line bioactivity was reconstituted in 20 mM Tris-HCl, pH 8.0, and re-chromatographed on the Mono Q column equilibrated with 20 mM Tris-HCl, pH 8.0 (FIG. 9). The column was eluted with 5 ml of equilibration buffer (20 mM Tris-HCl, pH 8.0) and developed at a flow rate of 1 ml/min with a 15 minute linear gradient from zero to 45% equilibration buffer containing 0.27M sodium chloride. This was followed by a 45 min shallow gradient from 45% to 60% equilibration buffer containing 0.36M NaCl; then a 10 min gradient from 60% to 100% buffer containing 0.6M sodium chloride; then 100% buffer containing 0.6M sodium chloride for 5 min, followed by a 12 min re-equilibration prior to the next run. The peak fraction 27–28 (MQ3-28B) and fractions 29–30 (MQ3-28C) were concentrated, dialyzed, and lyophilized as before.

Step 4

Figure 10A:
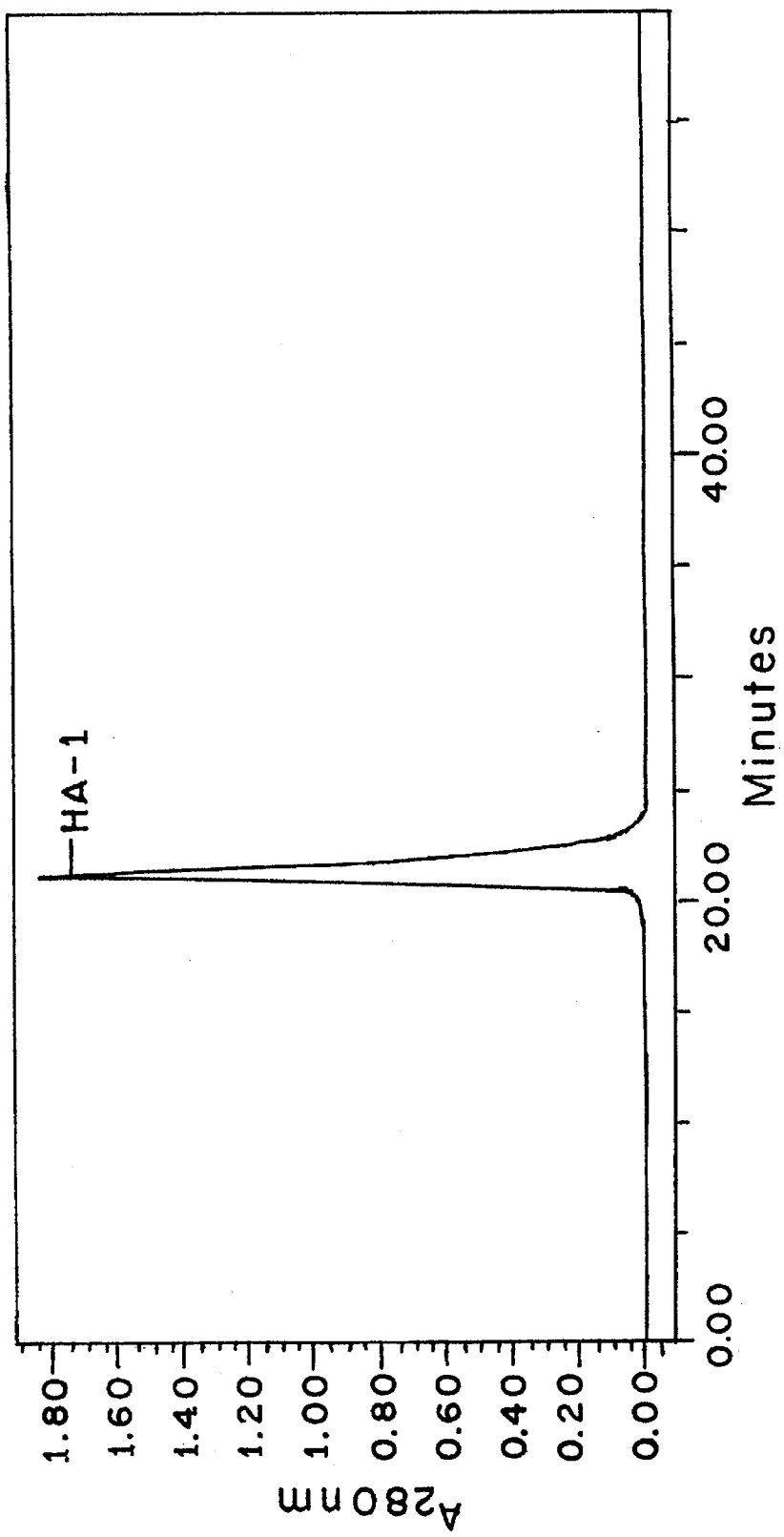
FIGS. 10A and 10B show the chromatographic elution profile of MQ3-28B (FIG. 10A) and MQ3-28C (FIG. 10B) on Shodex sizing column. HA-1 is shown in FIG. 10A; HA-2 is shown in FIG. 10B.
Figure 10B:
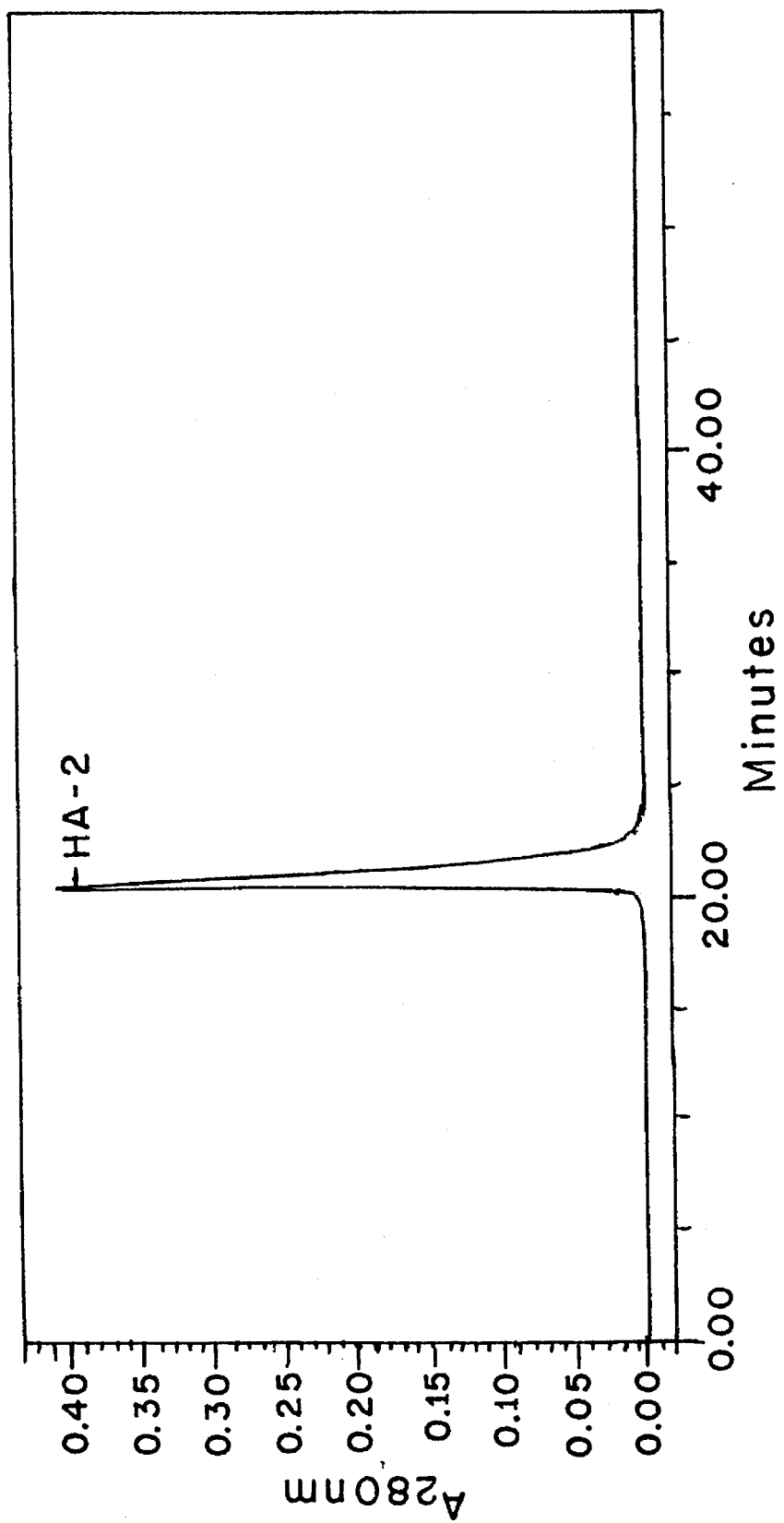

Chromatography on Shodex sizing column: The lyophilized bioactive fractions MQ3-28B and MQ3-28C from Step 3 that contained the tibial line activity were reconstituted in 0.05M sodium phosphate/0.1M sodium sulphate buffer, pH 7.5. To determine the purity of these peptides, the fractions were loaded on a Shodex PROTEIN KW-802.5 column (Waters, Milford, MA) equilibrated and eluted with the same buffer at a flow rate of 0.5 ml/min. The purified fraction obtained by running the MQ3-28B on the Shodex was designated as HA-1 (FIG. 10A), while the purified fraction obtained by running MQ3-28C on the Shodex column was designated as HA-2 (FIG. 10B). Both the purified fractions HA-1 & HA-2 were concentrated, dialyzed and lyophilized as before.

Protein Determination

The protein content of purified peptides HA-1 and HA-2 was determined by the method of Lowry, O. H., et al., *J. Biol. Chem.*, 193:265–274 (1951) with bovine serum albumin as the standard.

Tibial Growth Bioassay

The tibial line bioassay was performed according to the procedure described by Greenspan, F. S., et al., *Endocrinology*, 45:455–463 (1949). In brief, female rats were hypophysectomized at 40 days of age and were injected subcutaneously with human pituitary/plasma purified peptide fractions once a day for 4 days after a post operative period of 14 days. One day after the last injection, the animals were euthanized with $CO_2$, and the tibial growth plate was prepared for ocular micrometry (measurement of the plate width). Readings were done by two investigators on coded samples and averaged. Other similarly prepared rats were injected with a USDA bovine GH preparation that has a potency of 1.4 IU/mg protein. The response of the rat tibia to the bovine hormone standard was converted to that predicted with the human GH (potency 3.0 IU/mg protein) on the basis of the relative specific activities of the two hormone preparations. The rat tibia responds equally well to bovine GH or human GH. Tibial responses exceeding 25 μm in width of the cartilage plate compared to that of the control plate (saline injected animals) were considered significant. Sometimes tibial growth plates were marginally wider than the saline-injected controls. Some investigators (Greenspan, et al., *Endocrinology*, 45:455–463 (1949) and (Ellis, S., et al., 1978. *Recent Progress in Hormone Research*, 34:213–238) consider a response no greater than 25 μm above controls to be non-specific. In this work, we have therefore designated responses greater than 25 μm as Type I bioactivity; those greater than controls but less than 25 μm are designated Type II bioactivity. Samples having Type II activity may be so because insufficient material was injected. Extensive purification steps often resulted in only small quantities for analysis.

Enzyme Immunoassay for hGH

Samples of peptide fractions were analyzed by immunoassay. This is a chemical assay in which the amount of IGH is determined by comparison to a known concentration of hGH standard in the same assay. Data analysis yields IGH concentration expressed as nanograms IGH/ml sample. The "standard" GH preparation was obtained from Kabi Vitrum, Sweden and has a potency of 3.0 IU/mg protein. The immunoreactivity of the preparation was determined by the method of Farrington, M. A., et al., 1987. *Life Sciences*, 40:2479–2488 using Kabi hGH standard and hGH antiserum (Kabi Vitrum, Sweden).

Characterization of Purified Peptide

Molecular weight was estimated by gel filtration through a HPLC Superdex-75 HR 10/30 (10×300 mm) (Pharmacia-LKB Biotechnology) column following calibration with beta-amylase (200,000 MW), bovine serum albumin (66,000 MW), carbonic anhydrase (29,000 MW), ribonuclease (13,683 MW), caprotinin (6512 MW) and bacitracin (1400 MW) molecular weight standards (Pharmacia-LKB Biotechnology).

Reverse-Phase HPLC

Figure 8:
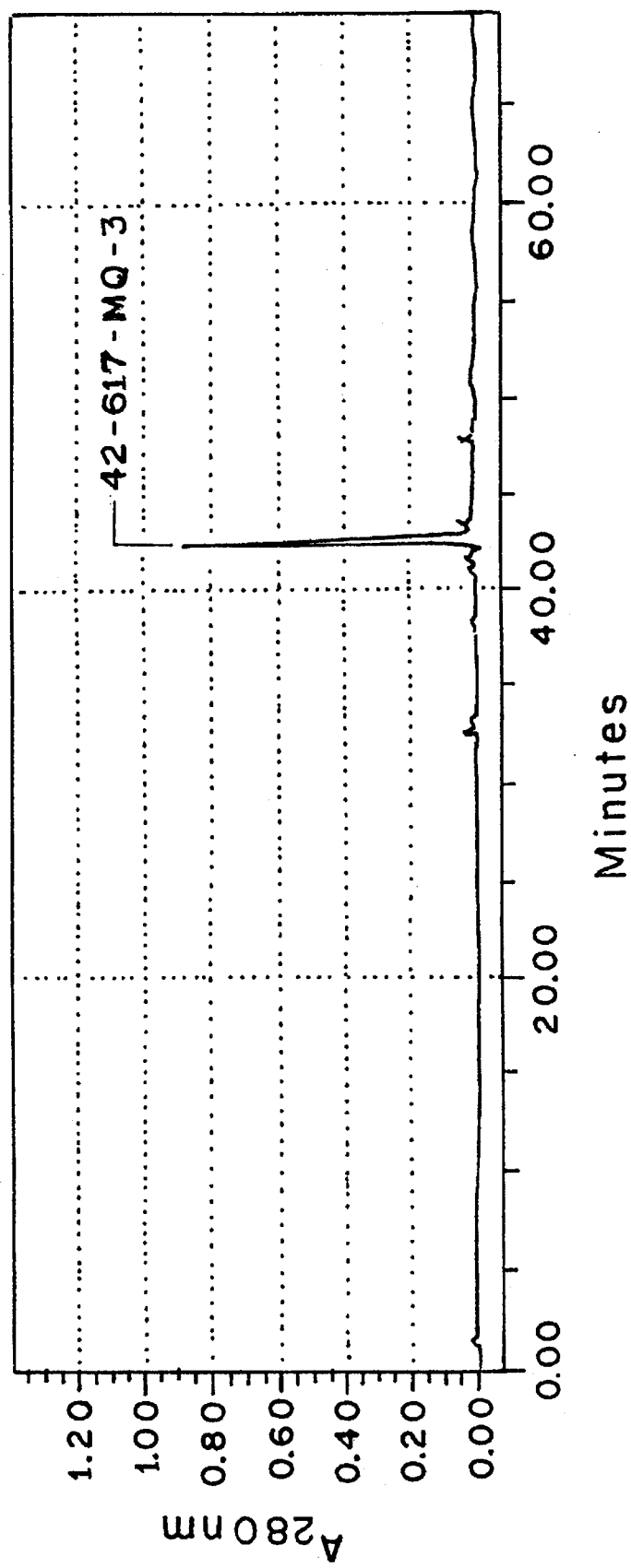
FIG. 8 shows a reverse phase elution profile of MQ-3 (FIG. 7) on Delta-pak C18 column showing a single symmetrical peak elution at 280 nm and minor contaminants.

Reverse-Phase chromatographic analysis of the purified peptide (FIG. 8) was performed using a Delta-Pak C18 column (39×150 mm) (Waters Millipore, Marlborough, Mass.). The tibial growth peptide fraction (MQ-3) was dissolved in aqueous 0.1% trifluoroacetic acid (TFA). The column was eluted at a flow rate of 1 ml/min with 5 ml of starting buffer (0.1% TFA in water) and developed with a 40 minute linear gradient to 100% acetonitrile containing 0.1% TFA (Buffer B), then 100% Buffer B for 10 min, followed by 15 minute re-equilibration prior to the next run. Absorbance was monitored at 280 nm.

Isoelectric Point

Figure 12:
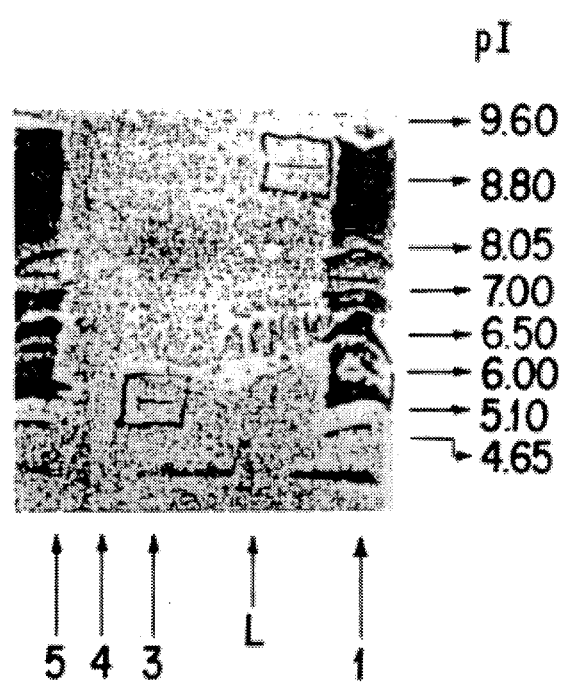
FIG. 12 shows the electrophoretic purity of tibial growth peptide. Isoelectric focusing (IEF) on a pH 3–9 gel. Lane 1: IEF standards; Lane 3: Fraction MQ-3 (from step 2); Lane 4: CFES fraction IV; Lane 5: IEF standards.

The isoelectric point (pI) of the tibial growth peptide (MQ3 from step 2) was determined by isoelectric focusing (IEF) using Phast System IEF method (Pharmacia-LKB Biotechnology) with a gel covering the pH range 3–9 (FIG. 12). The pI was determined by comparison to IEF standards.

Mass Spectrometry

Mass spectrometric analysis was done to determine the molecular weight of purified growth potentiating peptides HA-1 and HA-2 and was performed by Wistar Micro-sequencing Laboratory, (Philadelphia, Pa.).

Amino Acid Composition

Amino acid composition of the purified tibial growth potentiating peptides HA-1 and HA-2 was performed by Wistar Protein Micro-sequencing laboratory (Philadelphia, Pa.).

Sequence Analysis

Amino acid sequence determination of the tibial potentiating peptides was performed using an automatic Edman HP Sequencer.

Results:

FIG. 1 outlines the procedure used for the purification of tibial growth potentiating peptides from human pituitaries.

When the pituitary homogenate was electrophoresed (CFES), the majority of the protein migrated to regions defined as Fraction I and II (FIGS. 2A and 2B). This pattern of separation on CFES was reproducible and repeatable (6–8 batch runs). The major percentage (53–67%) of the tibial growth activity as determined by tibial line bioassay (FIG. 3A) was recovered in the most anodal fraction (fr. 71–100). This anodal fraction was devoid of any GH immunoreactivity as measured by enzyme immunoassay (FIG. 3B). Total recovery of the tibial growth potentiating activity after the CFES run was between 94–191%.

Figure 4A:
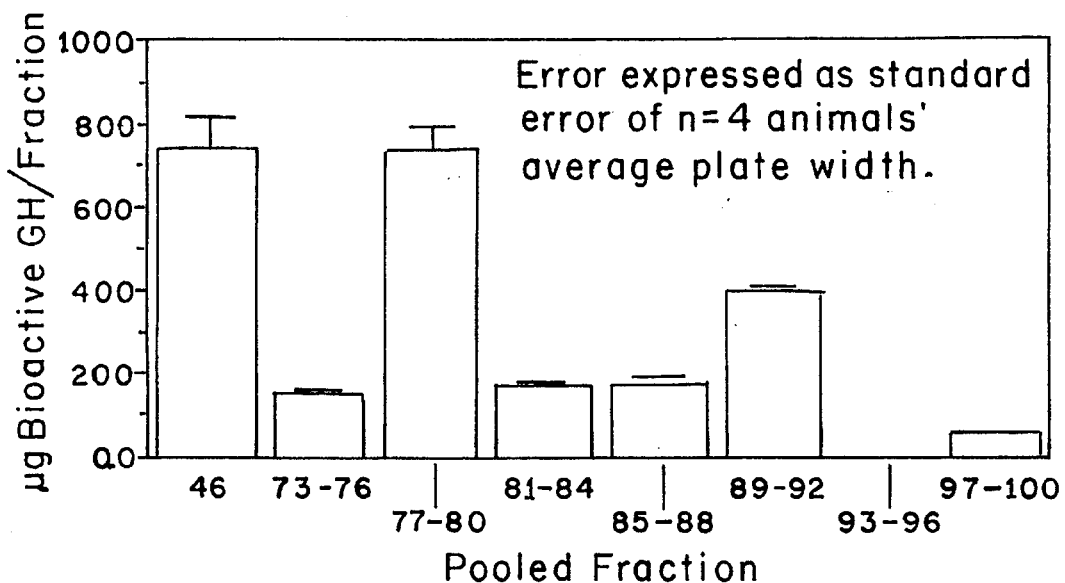
FIG. 4A shows the amount of bioactivity as measured by tibial line bioassay in various pooled continuous flow electrophoresis fractions and FIG. 4B shows the amount of bioactive growth hormone expressed on a protein basis in the same pooled fractions.
Figure 4B:
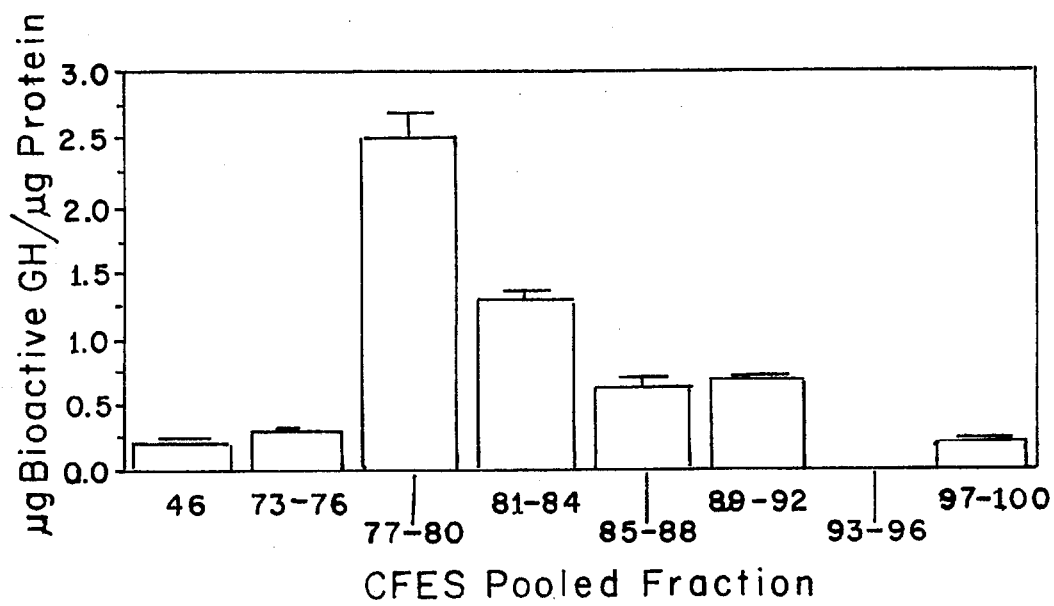
Figure 5:
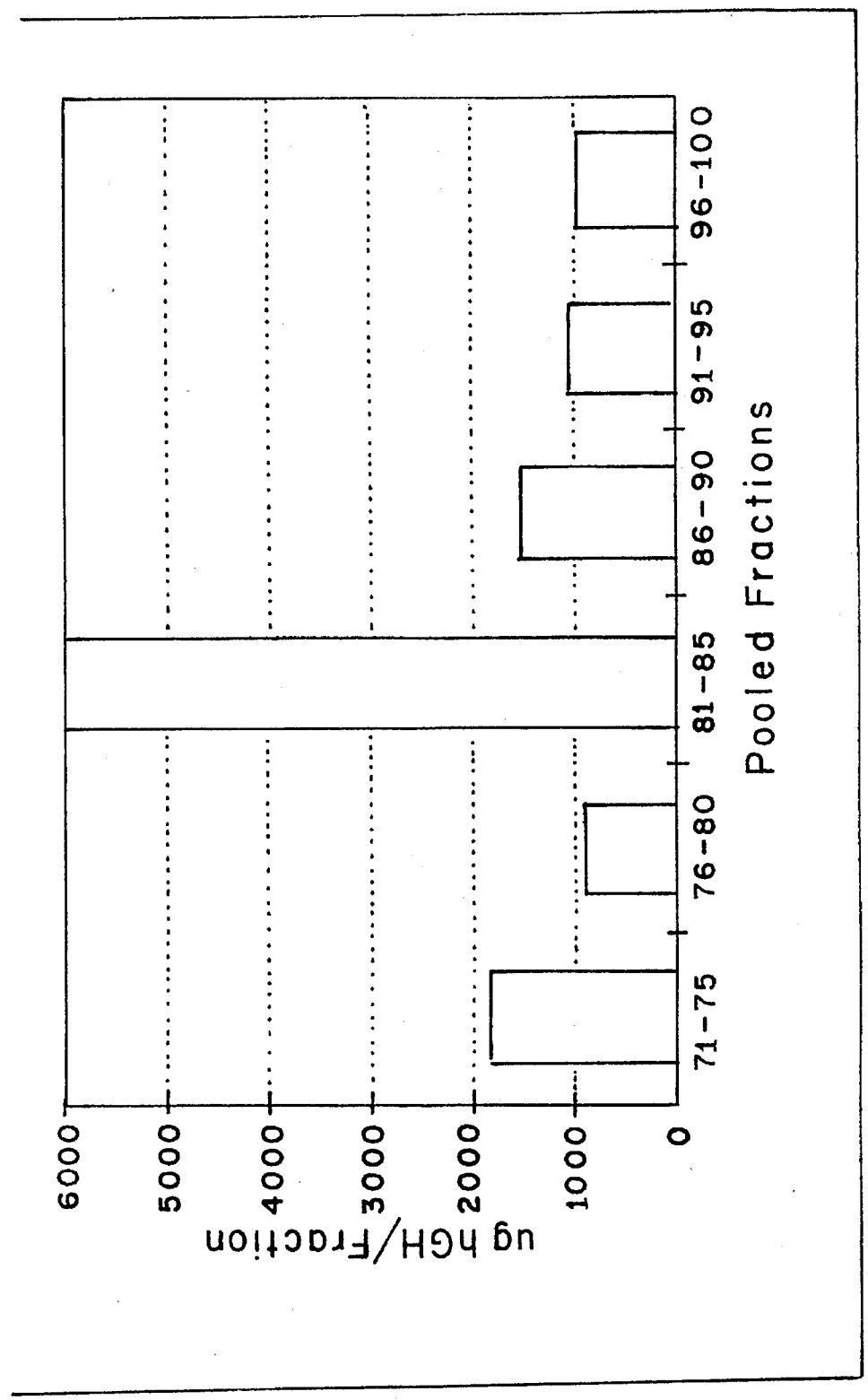
FIG. 5 shows the distribution and localization of tibial growth potentiating peptides in the anodal fractions after continuous flow electrophoresis.
Figure 6A:
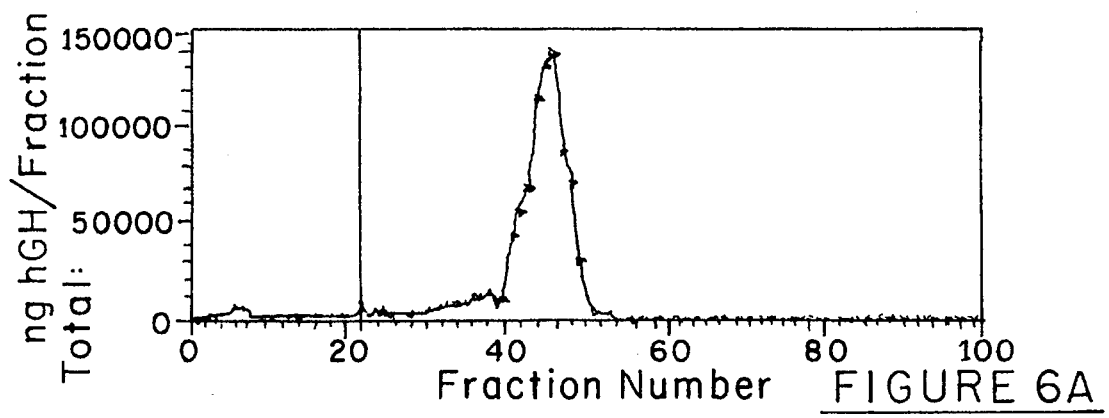
FIGS. 6A, 6B, 6C, and 6D show the stability of the continuous flow electrophoresis unit during the operation of separating proteins from a human pituitary homogenate.
Figure 6B:
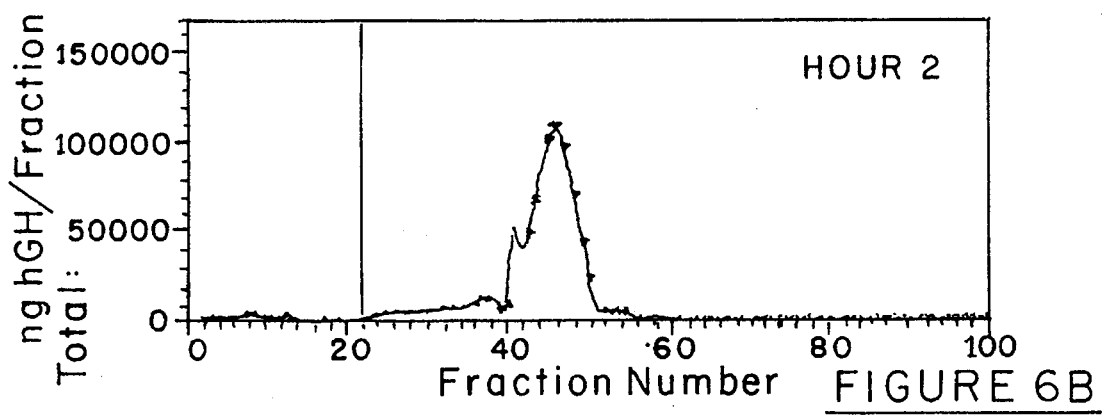
Figure 6C:
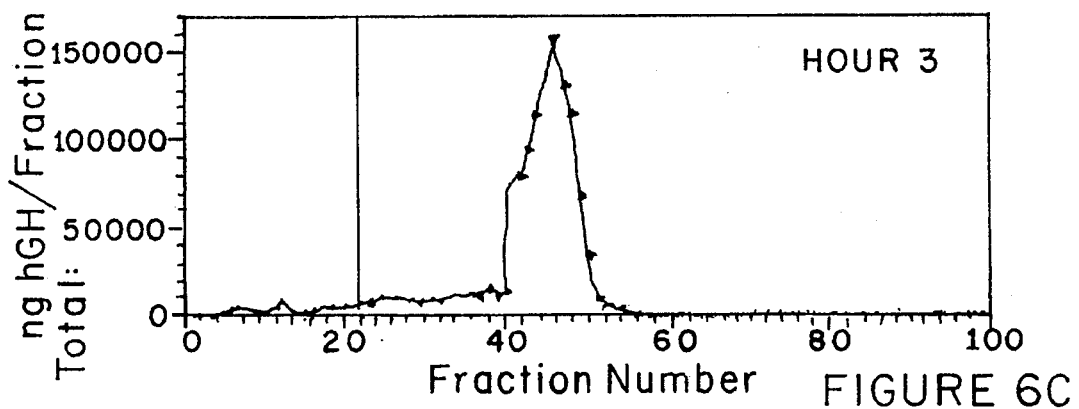
Figure 6D:
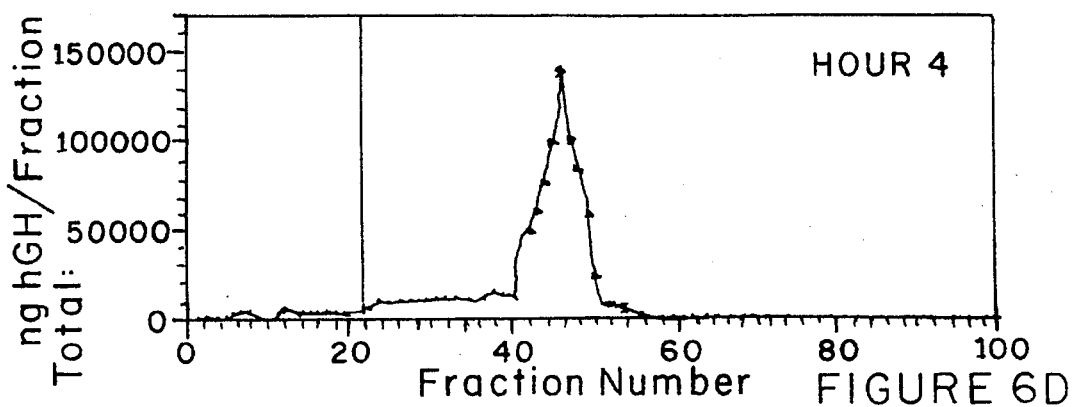

Attempts to localize the biologically active material to smaller regions within CFES fraction IV (i.e. 73–100) indicate that it may be possible to do so. For example, in one experiment, fractions 77–80 and 89–92 were enriched in bioactivity (FIG. 4A), and on a protein basis, the material in fraction 77–80 was 10 times higher than the monomeric hGH in fraction 46 (FIG. 4B). In another experiment, the fraction containing the greatest amount of bioactive material was in Fraction 81–85 (FIG. 5). Taken together, the results from FIGS. 4 and 5 show that it will be possible to further localize the tibial growth potentiating activity by CFES. In these studies, we have chosen to use the entire CFES fraction IV material for further purification of the tibial growth potentiating peptides. Growth potentiating activity in CFES fractions I, II and III were not analyzed further in this study.

If the free flow electrophoresis processing procedure will ever be adapted for the purification of pituitary tibial growth potentiating peptides, the process must be stable and therefore reproducible. Stability of the electrophoresis processing procedure is documented by data shown in FIGS. 6A, 6B, 6C and 6D. Note that the peak fractions (43–45) containing immunoreactive hGH from the human pituitary were reproducible during the four hours of running. These data support the claim that electrophoresis processing by free flow methodology is stable. In fact, the data shown in FIG. 7 were obtained after continuous CFES processing for 24–48 hours to obtain sufficient material for further purification by HPLC.

FIG. 7 depicts the elution profile of the concentrated CFES anodal fraction IV (fr. 71–100) applied to a HPLC anion exchange column. This step yielded 6 fractions. Tibial growth potentiating activity was found in peak 3 (MQ-3). The results of four separate tibial line assays of step 2 HPLC Mono Q Fr. 3 (MQ-3) material obtained from three different batches of human pituitary extracts show tibial growth activity (Table 1). Tibial responses were proportional to amount of material injected (Assay #2 in Table 1).

TABLE 1

BIOASSAY OF FRACTION MQ-3 (STEP II)

| | PROTEIN µG | VOL µL | TIBIAL WIDTH (µM) | BIOACTIVITY TYPE | hGH µG | µG hGH/mg protein |
|---|---|---|---|---|---|---|
| Assay #1 | Control | — | 176 | — | — | — |
| | 2.91* | 100 | 187 | Type II | 10.76 | 3697 |
| Assay #2 | Control | — | 153 | — | — | — |

TABLE 1-continued

BIOASSAY OF FRACTION MQ-3 (STEP II)

| | PROTEIN µG | VOL µL | TIBIAL WIDTH (µM) | BIOACTIVITY TYPE | hGH µG | µG hGH/mg protein |
|---|---|---|---|---|---|---|
| | 2.10* | 100 | 181 | Type I | 9.56 | 4552 |
| | 4.20* | 200 | 210 | Type I | 18.29 | 4355 |
| Assay #3 | Control | — | 138 | — | — | — |
| | N.D.** | 500 | 215 | Type I | 20.56 | N.D. |
| Assay #4 | Control | — | 149 | — | — | — |
| | 0.52 | 25 | 180 | Type I | 9.24 | N.D. |

*HPLC pooled fraction, concentrated and lyophilized
**HPLC pooled fraction, not concentrated, lyophilized
n = 1 or 2 rats/group MQ-3 eluted at a molar concentration of 0.33–0.35M NaCl in Tris-HCl buffer, pH 8.0 with a retention time of 45.38 minutes. The percentage recovery of bioactive material from this single HPLC step was 56%.

Reverse phase chromatography of peptide MQ-3 resulted in a single symmetrical peak (FIG. 8) eluting with a retention time of 42.6 minutes. Because minor contaminants are present in MQ-3, further purification of MQ-3 was done by re-chromatography on the Mono-Q anion exchange column using a more shallow gradient.

After re-chromatography a major peak (MQ3-28B) eluting at a molar concentration of 0.29M NaCl in Tris-HCl buffer, pH 8.0, with a retention time of 27.683 minutes and a minor component (MQ3-28C) with a retention time of 28.40 in the trailing edge of the major peak was found (FIG. 9). In order to separate and purify MQ3-28B from MQ3-28C, material collected between retention times 26.0 and 27.9 minutes or 28.0 and 29.9 minutes from the ion exchange column was pooled and each pool was run separately on a Shodex sizing column. Material from MQ3-28B, eluting with a retention time of 21.05 minutes, was designated as HA-1. Material from MQ3-28C eluted with a retention time of 21.03 minutes and was designated as HA-2. On the basis of elution times alone the material in HA-2 would be expected to be smaller than that in HA-1 by 40 daltons. Tibial growth promoting activity was detected in both MQ3-28B and MQ3-28C (Table 2). Material in MQ3-28C had type I bioactivity; that in MQ3-28B had type II activity. The 10 fold difference in protein injected into the assay animals may explain the lower response in MQ3-28B material.

TABLE 2

STEP III FRACTIONS:

| SAMPLE | PROTEIN µG | TIBIAL WIDTH (µM) | BIOACTIVITY TYPE | hGH µG | µG hGH/mg protein |
|---|---|---|---|---|---|
| Control | — | 145 | — | — | — |
| MQ3-28B | 2.62 | 153 | Type II | 2.58 | 985 |
| MQ3-28C | 27.70 | 172 | Type I | 8.21 | 296 | n = 2 rats/group

Figure 11:
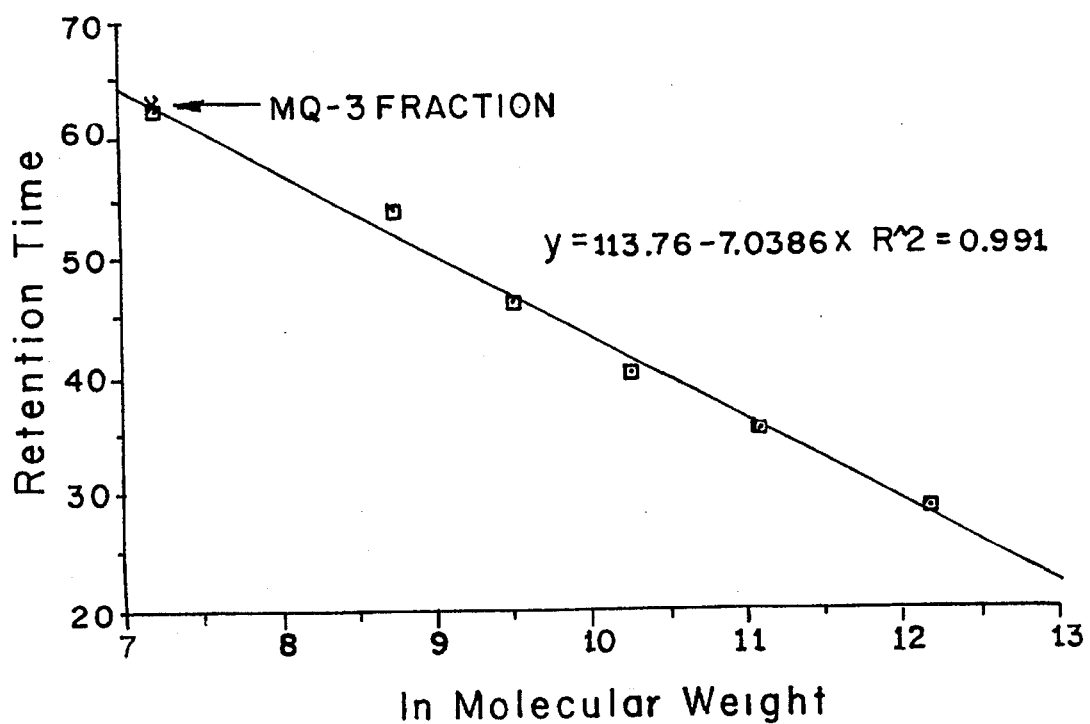
FIG. 11 shows the results of a gel filtration run to estimate the molecular weight of TGPP using known protein molecular weight standards.

Gel filtration of MQ-3 fraction from step 2 on a calibrated HPLC high performance Superdex-75 column (0.5 ml/min flow rate) equilibrated with 0.1M potassium phosphate buffer (pH 7.0) implied an apparent molecular weight of less than 5000 daltons for the peptide. The column void volume was determined with beta-amylase. The Ve-Vo ratio of HA-1 was 2.19, while the ratio for molecular weight standards obtained with the same column were 1.23 for bovine serum albumin, 1.40 for carbonic anhydrase, 1.61 for ribonuclease, 1.88 for aprotinin and 2.17 for bacitracin (FIG. 11). These results indicate that this tibial growth peptide fraction containing both HA-1 and HA-2 is not the same as traditional human growth hormone (22K) because of its low molecular size.

Isoelectric focusing of peptide MQ-3 revealed a single major component with a pI of 5.1 (FIG. 12). No evidence of microheterogeneity of the tibial growth peptide at this stage of purification was observed. Although this tibial growth peptide differs in its molecular size from that of the monomeric growth hormone (22K), the pI of this tibial growth potentiating peptide closely resembles the pI of human monomeric growth hormone (5.1–5.6). However, it differs from that of the 5K peptide isolated from the N-terminus of hGH which has an alkaline pI (Singh, R. N., et al., *J. Protein Chemistry*, 2(6):425–436 [1983]).

Mass Spectrometry

Figure 13:
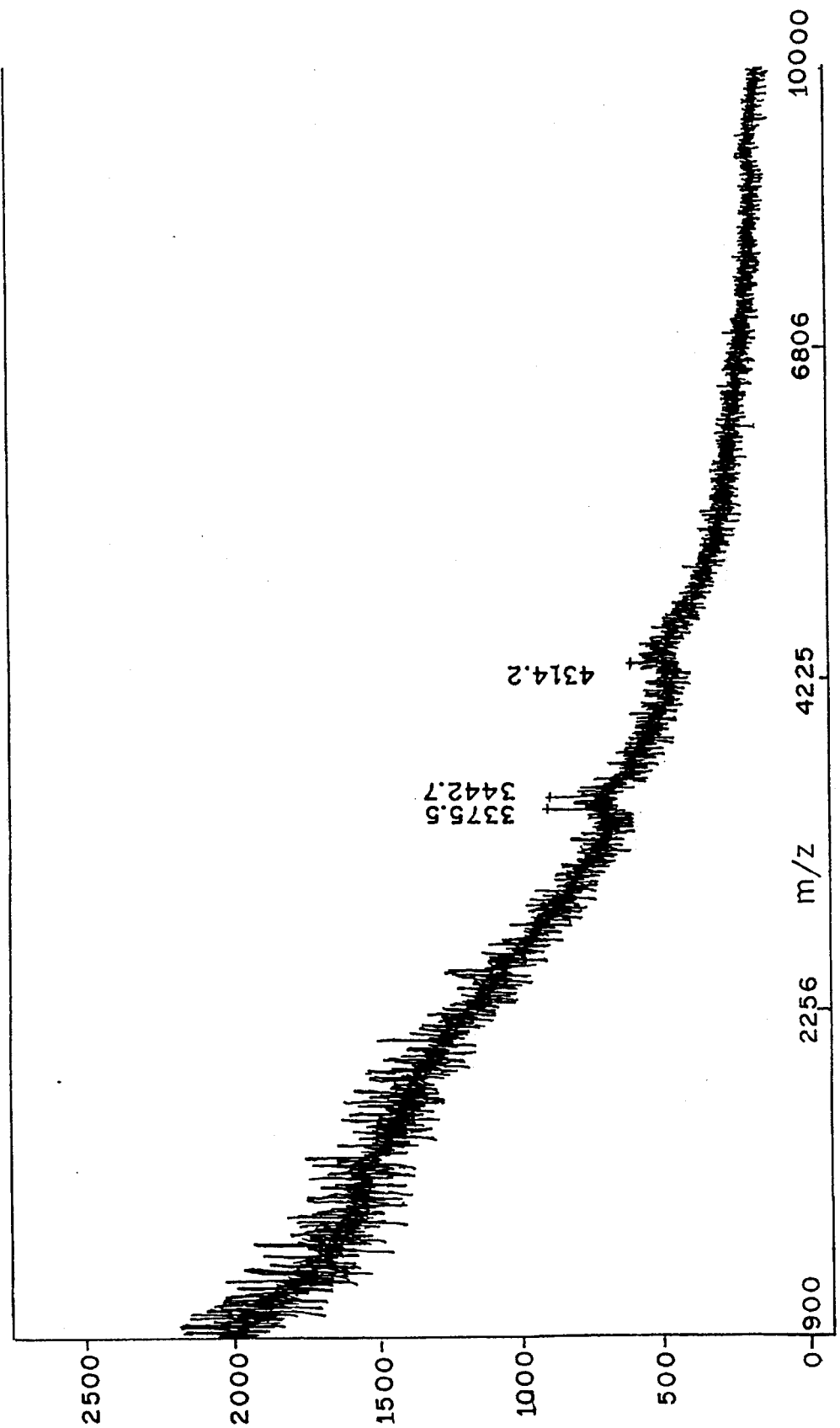
FIGS. 13 and 14 show the molecular weight estimation of peptides HA-1 and HA-2 by mass spectrometry.
Figure 14:
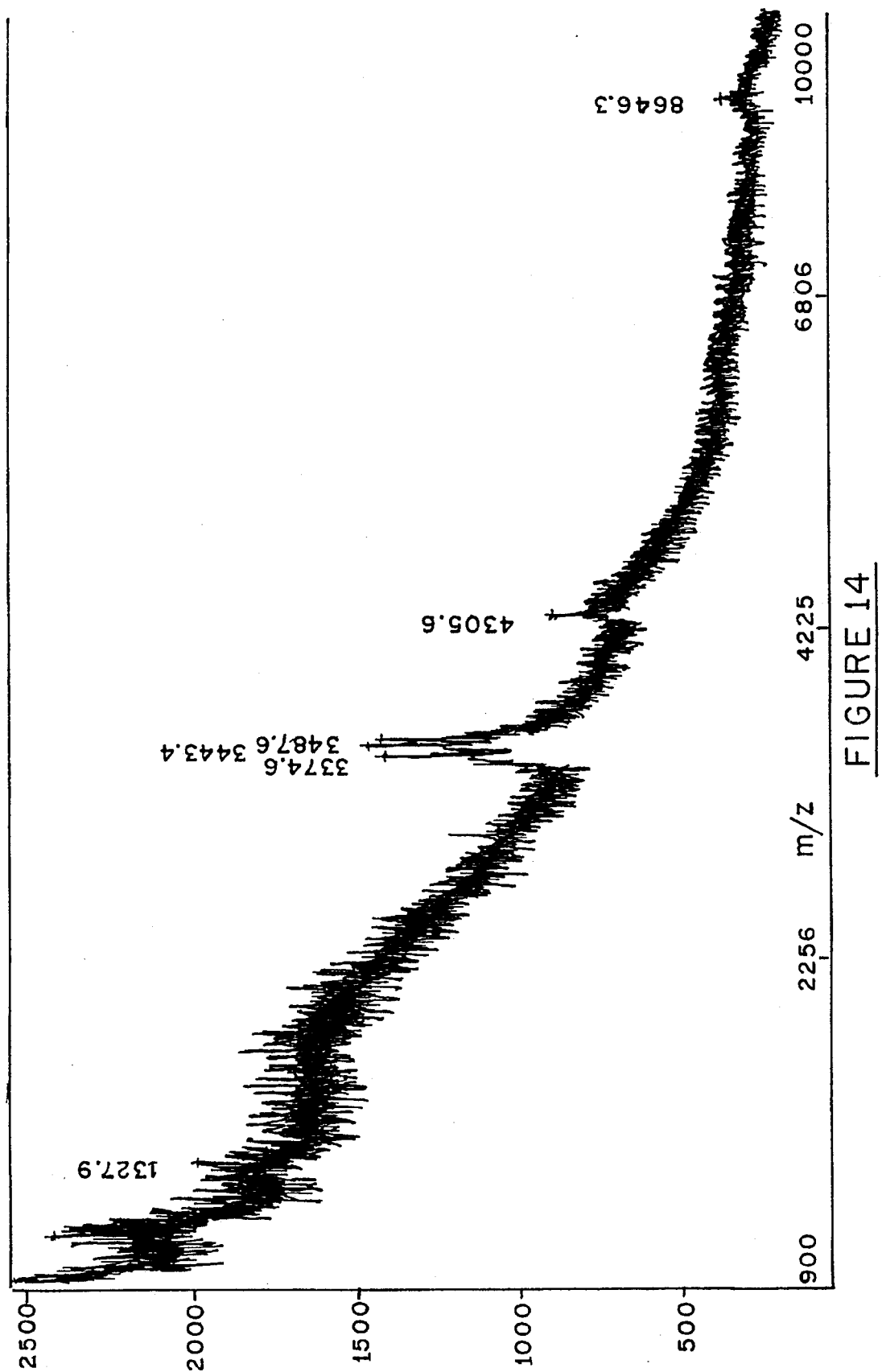

The molecular weight of tibial growth potentiating peptides HA-1 and HA-2, assessed by mass spectrometry, indicates that they have a molecular weight range of 3374–4314 (FIGS. 13 and 14). The double/triplet signal may represent one peptide species that is chemically heterogeneous due to post translational modifications. Further, the 8646 signal may be a dimer of the 4306 peptide.

Amino Acid Composition

Figure 15A:
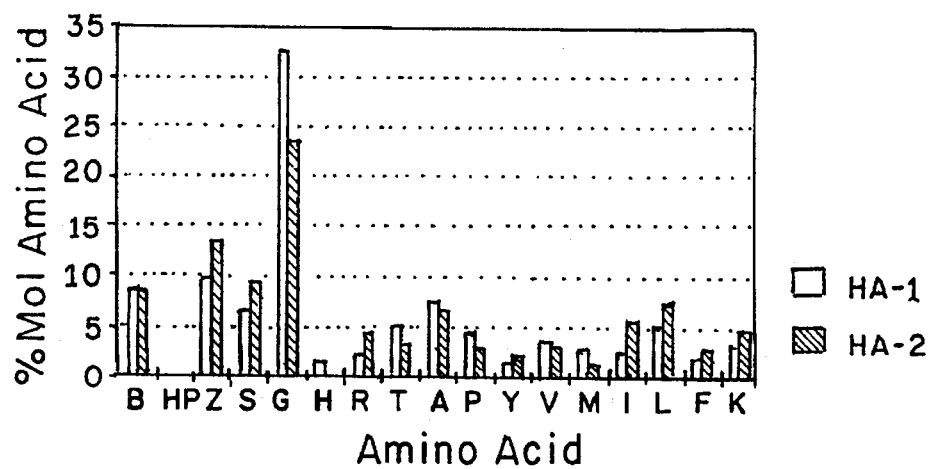
FIG. 15A shows the amino acid composition of purified growth potentiating peptides HA-1 and HA-2.
Figure 15B:
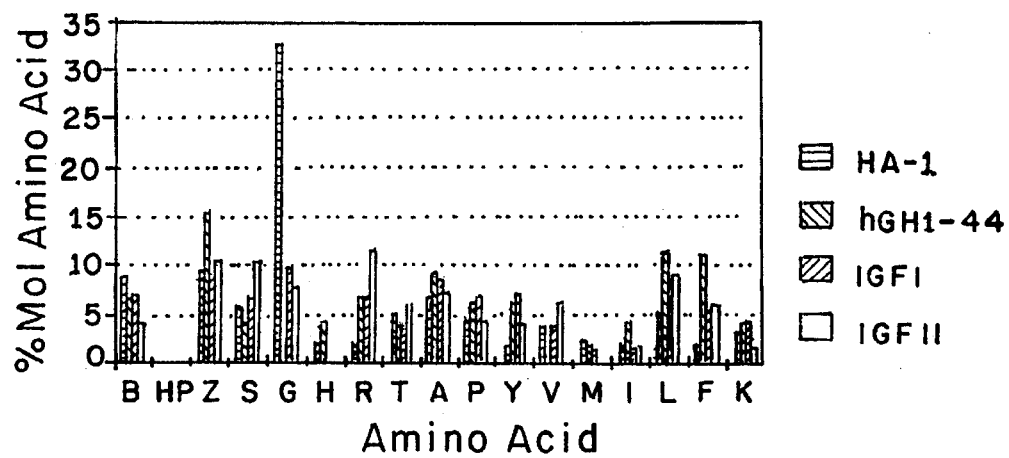
FIGS. 15B and 15C show the amino acid compositions of HA-1 and HA-2, respectively, in comparison to 1–44K peptide of human growth hormone, IGF I and IGF II.
Figure 15C:
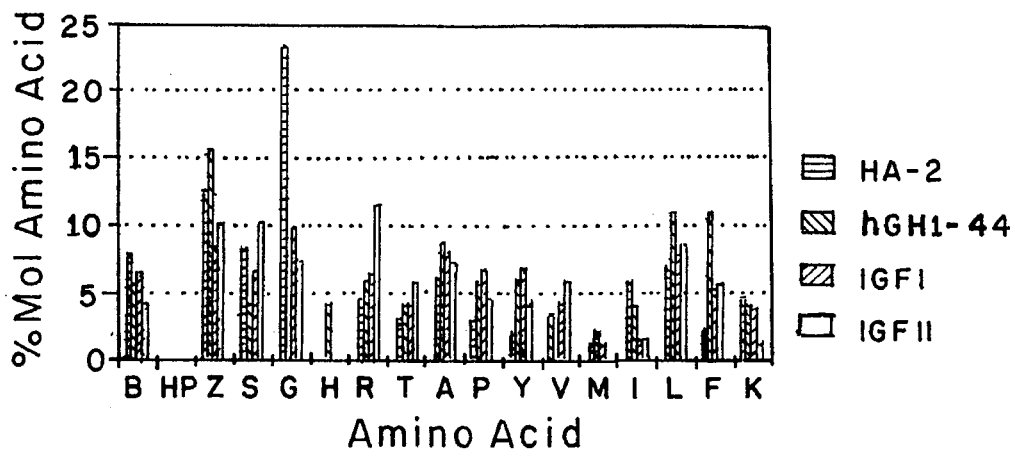

The amino acid compositions of HA-1 and HA-2 are shown in Table 3 and FIG. 15.

TABLE 3

| AMINO ACID CODE | AMINO ACID | PEPTIDE HA-1 % MOL ± SE | PEPTIDE HA-2 % MOL | 1-44 hGH % MOL | IGF I % MOL | IGF II % MOL |
| --- | --- | --- | --- | --- | --- | --- |
| B  | ASX  | 8.06 ± 1.11  | 8.3  | 6.8  | 7.1  | 4.5 |
| HP | HPRO | 0.0 ± 0.0    | 0.0  | 0.0  | 0.0  | 0.0 |
| Z  | GLX  | 9.46 ± 1.48  | 13.5 | 15.9 | 8.6  | 10.4 |
| S  | SER  | 6.6 ± 1.20   | 9.2  | 4.5  | 7.1  | 10.4 |
| G  | GLY  | 33.0 ± 12.7  | 23.8 | 0.0  | 10.0 | 7.5 |
| H  | HIS  | 1.7 ± 0.0    | 0.0  | 4.5  | 0.0  | 0.0 |
| R  | ARG  | 2.46 ± 0.38  | 4.7  | 6.8  | 7.1  | 11.9 |
| T  | THR  | 5.33 ± 0.82  | 3.7  | 4.5  | 4.3  | 6.0 |
| A  | ALA  | 7.36 ± 1.47  | 6.8  | 9.1  | 8.6  | 7.5 |
| P  | PRO  | 4.7 ± 0.7    | 3.0  | 6.8  | 7.1  | 4.5 |
| Y  | TYR  | 1.93 ± 0.48  | 2.6  | 6.8  | 4.3  | 4.5 |
| V  | VAL  | 4.2 ± 1.0    | 3.6  | 0.0  | 4.3  | 6.0 |
| M  | MET  | 2.73 ± 2.2   | 1.3  | 2.3  | 1.4  | 0.0 |
| I  | ILE  | 2.5 ± 0.60   | 6.1  | 4.5  | 1.4  | 1.5 |
| L  | LEU  | 5.76 ± 1.43  | 7.7  | 11.4 | 8.6  | 8.9 |
| F  | PHE  | 2.1 ± 0.64   | 2.8  | 11.4 | 5.7  | 6.0 |
| K  | LYS  | 3.46 ± 0.88  | 4.9  | 4.5  | 4.3  | 1.5 |

Values in Table 3 represent the mean % mole amino acid plus or minus standard error for 3 separate trials for peptide HA-1 and the average of 2 trials for peptide HA-2. The results indicate good correspondence in amino acid composition between the 2 peptides. They also show reproducibility of the amino acid composition from the different batches. Differences in amino acid composition between molecules in the IGF family and the N terminal fragment (1–44) of hGH obtained from published data show that neither HA-1 or HA-2 are derived from these growth peptides. The fact that 1) the molecular weights of the N-terminal hGH fragment, IGF-I and IGF-II are 6131, 7988, and 6898 respectively are different and 2) that our preliminary amino acid sequence data show total uniqueness (see below) further supports this view.

Sequence Analysis

Preliminary analysis of the step III peptide fraction containing both HA-1 and HA-2 yielded 25 amino acid residues with the first eight residues yielding inconclusive data as shown in Table 4.

TABLE 4

| RESIDUE | AMINO ACID, pmoles |
| --- | --- |
| 1  | X |
| 2  | X          P |
| 3  | Q, 12 |
| 4  | X          P |
| 5  | N, 11.5 |
| 6  | P, 11+     L, 1.0 |
| 7  | S, 2.1     R, 1.9 |
| 8  | P, 8+      W, 1.1    V, 1.1    L, 1.2 |
| 9  | A, 8.4 |
| 10 | S, 1.5 |
| 11 | P, 4.4 |
| 12 | V, 4.6 |
| 13 | V, 4.5 |
| 14 | V, 4.5 |
| 15 | G, 5.2 |
| 16 | G, 5 |
| 17 | G, 5 |
| 18 | A, 3.4 |
| 19 | S, 0.8 |
| 20 | L, 3.1 |
| 21 | P, 2.0 |
| 22 | E, 2.4 |
| 23 | F, 2.0 |
| 24 | X |
| 25 | Y, 2.4 |

TABLE 4-continued

| RESIDUE | AMINO ACID, pmoles |
| --- | --- |

(1) High background in early cycles indicates possible contamination of sample with amino acids or small peptides.
(2) Sample also contains at least 3+ low level sequences - see cycle 8.
(3) High amino acid background in late cycles indicates presence of significant amounts of protein.
(4) Due to possible contamination, the reported sequence is tentative, especially in early residues.
(5) Major component is greater than 25 residues.
(6) Residue 24 could be modified cysteine.

The above sequence is distinct from the sequence residues of the hGH (Baumann G., 1991. *Endocrine Reviews*, Vol. 12(4):424–449) as well as the 5K peptide reported by Singh, R. N., et al. 1983. *J. Protein Chemistry*, 2(6):425–436. The results indicate that HA-1/HA-2 has the following sequence from residues 1–25:

X Pro Gln Pro Asn Pro Ser Pro Ala Ser Pro Val Val Val Gly Gly Gly Ala Ser Leu Pro Glu Phe X Tyr (SEQ. ID. NO. 1)

However, after considering the possible contamination, it is concluded that the peptide has the following partial amino acid sequence from residues 9–25

Ala Ser Pro Val Val Val Gly Gly Gly Ala Ser Leu Pro Glu Phe X Tyr (SEQ. ID. NO. 2)

Because the above sequences are unique it is concluded that TGPP is not caused by proteolysis of 22K hGH.

Additional information of HA-1 and HA-2 peptides: Amino acid sequence determinations were attempted twice for both peptide HA-1 and HA-2 (two different batches). There was no signal in any cycle. It is possible that the purified peptides at this stage are N-terminally blocked.

Microdigestion

Micro-digestion of HA-1 and HA-2 was attempted in order to obtain fragments to search for amino acid clusters. Digestions of peptides HA-1 and HA-2 were performed using trypsin (0.05mg) in 50 mM ammonium bicarbonate buffer at room temperature for various times. Mass spectrometry and HPLC analyses using reverse phase C18 columns were performed on the digests.

Conclusions

1). Mass spectrometry indicated incomplete digestion. 2). The bioactive component most probably was represented by the series of peaks between molecular weights 3300–3500. This peptide may migrate heterogeneously on reverse phase, possibly due to conserved conformations. 3). HA-1 and HA-2 adsorb to surfaces; this results in losses during preparation and low recoveries. 4). The peptides are like a "brick" because they digest very slowly with trypsin, even under aggressive conditions. Most of the remaining undigested peptide may represent a tightly preserved conformation (possibly held together by disulfide bonds).

EXAMPLE 2

Isolation Growth Peptides from Human Plasma

Extraction

Frozen cryo poor human plasma (HP) was obtained over dry ice from Baxter Health Care Corporation, Los Angeles, Calif. A total of 4 to 5 batches of 250 ml to 2 liters of cryo poor plasma were utilized in these studies. The HP was thawed overnight at 4° C., filtered through 24 layers of cheese cloth to remove any residual coagulated material, and diluted to 58% with 0.001M ammonium bicarbonate buffer. This 58% plasma fraction was extracted by slow addition of an equal volume of 95% chilled ethanol with constant stirring; extraction continued overnight at 4° C. for 16 to 24 hours.

The precipitated proteins/peptides were removed either by filtration on Whatman No. 41 paper or by centrifugation at 12,500×g for 40 minutes at 4° C. The sedimented precipitated pellet was removed with a metallic spatula and washed with four volumes of 250 ml of acetone by passing through a buchner funnel fitted with Whatman No. 41 filter paper. The precipitate was dried at room temperature on aluminum foil for about 3 to 4 hours to obtain the alcohol/acetone dry powder (ACP) which contained the proteins/peptides.

The ACP was dissolved in 0.001M ammonium bicarbonate buffer with constant stirring overnight at 4° C. The solution was centrifuged at 47,800×g for 40 minutes at 4° C. to remove debris.

Ultrafiltration/Hollow Fiber Concentration

The 47,800×g supernate was concentrated on an Amicon RA2000 (model CH2PRS, Amicon, Beverly, Mass.) fitted with a 30,000 MWCO hollow fiber cartridge. The filtrate containing proteins and peptides of less than 30,000 MW was collected and further concentrated on a hollow fiber cartridge with a 10,000 MWCO. The filtrate containing proteins/peptides of less than 10,000 MW was further processed on an Amicon cell (model 2000, Amicon, Beverly, Mass.) fitted with a 1000 MW cut off PLAC membrane (Millipore, Bedford, Mass.). The concentrated retentate containing 1–10K proteins/peptides was dialyzed in 0.001M ammonium bicarbonate buffer and lyophilized. This lyophilized 1–10K protein/peptide fraction was used for the purification of tibial growth potentiating peptides.

Purification

All operations except HPLC were performed at 4° C. unless otherwise noted. HPLC was performed at laboratory ambient temperatures (about 22° C.) on Waters HPLC 600 E system (Waters, Milford, Mass.).

HPLC-Step 1

Figure 17A:
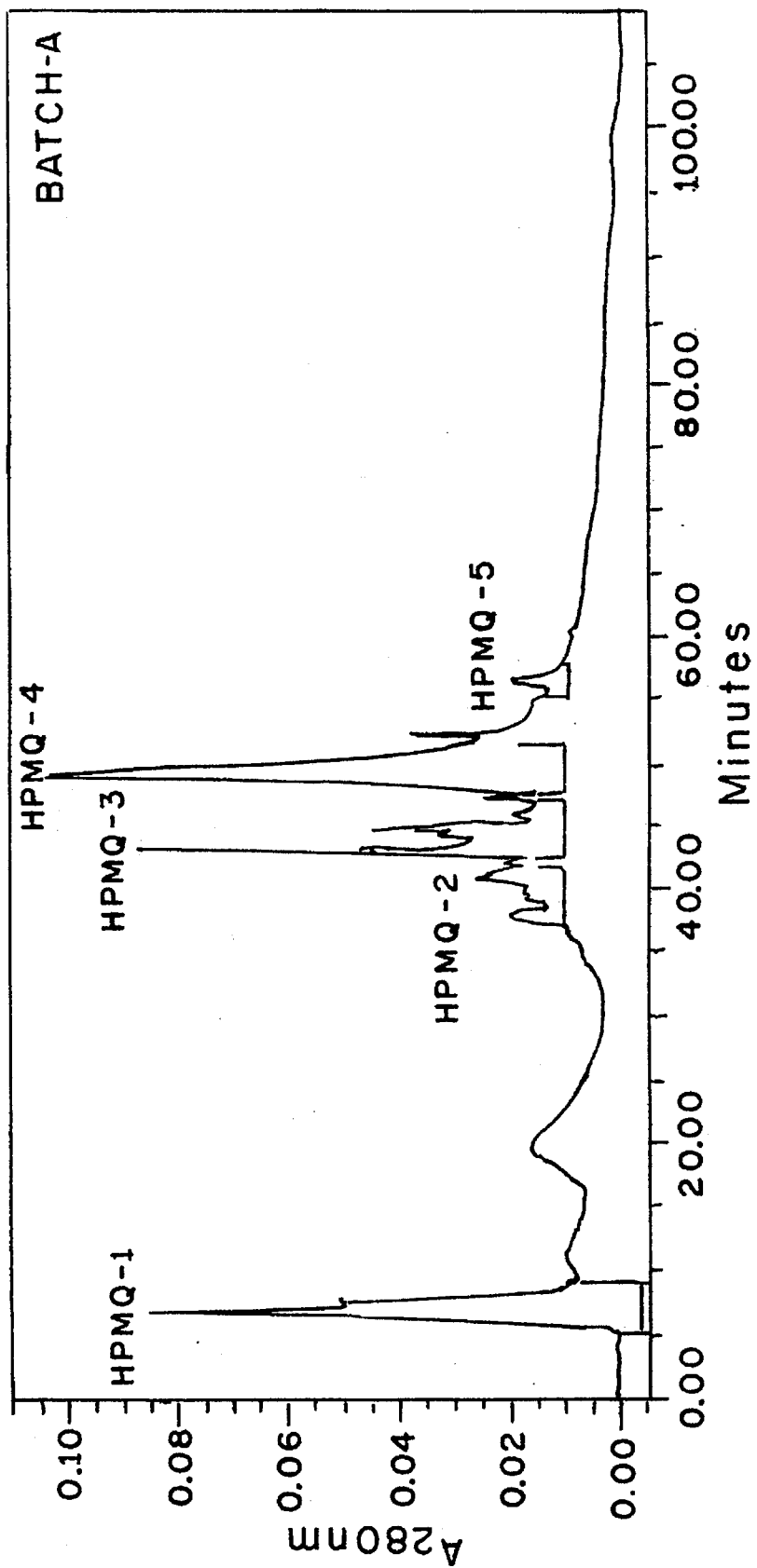
FIGS. 17A and 17B show chromatographic elution profiles of human plasma 1–10K protein/peptide obtained from two batches (batches A and B, respectively) of human plasma.
Figure 17B:
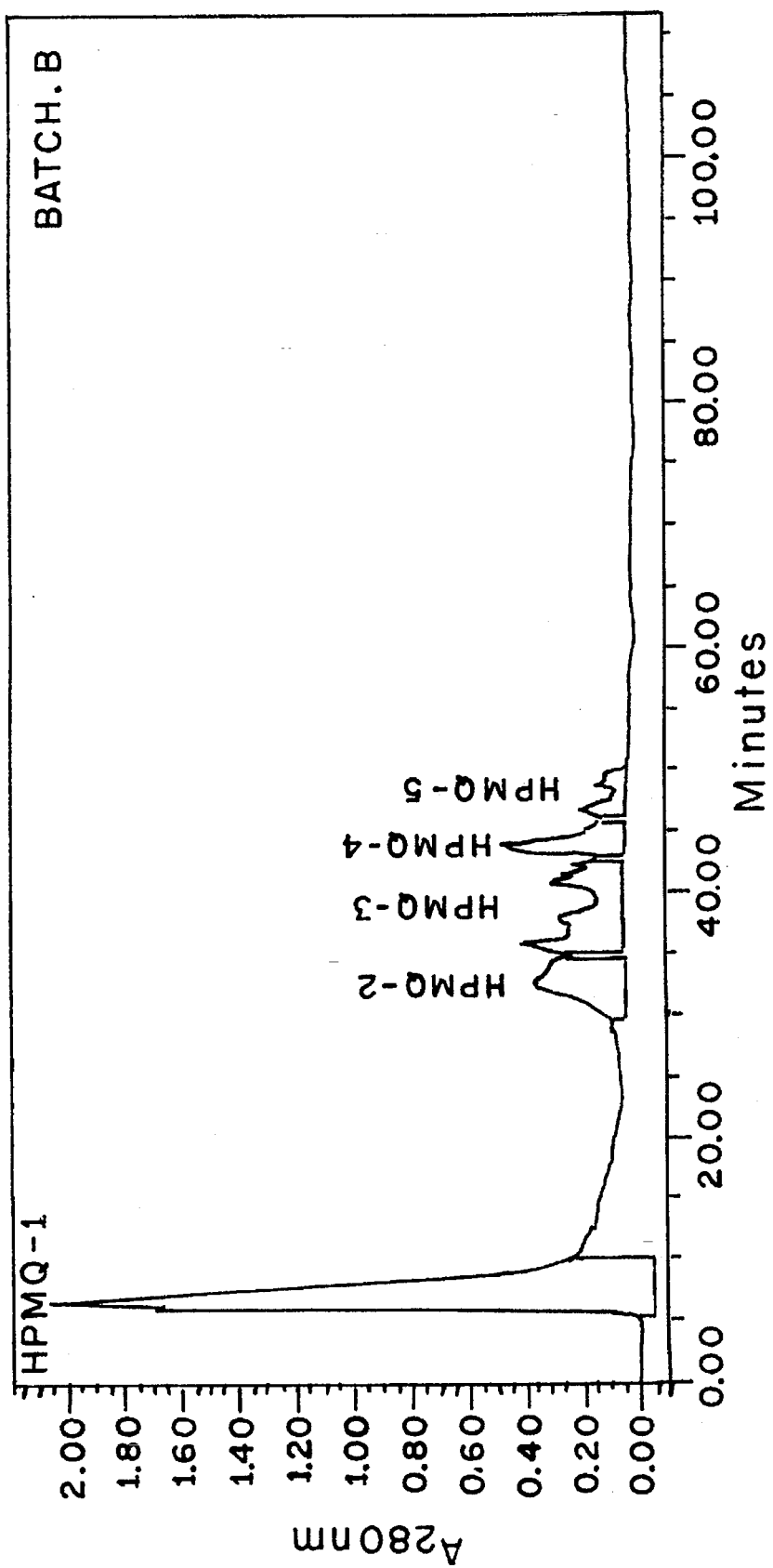

The pooled, lyophilized plasma 1–10K protein/peptide fraction was reconstituted in 20 mM Tris-HCl buffer, pH 8.0, and applied to an anion exchange column (Mono Q, HR 10/10 column; Pharmacia-LKB Biotechnology). equilibrated with 20 mM Tris-HCl, pH 8.0 (FIG. 17A—Batch A and FIG. 17B—Batch B). The column was eluted with 20 ml of 20 mM Tris-HCl, pH 8.0, and developed at a flow rate of 1 ml/min with a 50 minute linear gradient from zero to 100% 20 mM Tris-HCl buffer, pH 8.0 containing 0.6M sodium chloride, then 100% Buffer containing 0.6M sodium chloride for 20 minutes, followed by 22 min re-equilibration before the next run. Protein was monitored throughout purification by measuring the absorbance at 280 nm. Fractions were pooled from the Batch B, 1–10K protein/peptide run as follows: HPMQ-1 (fr. 6–10), HPMQ-2 (fr. 29–34), HPMQ-3 (fr. 35–42), HPMQ-4 (fr. 43–46) and HPMQ-5 (fr. 47–57). These fractions were concentrated, dialyzed on an Amicon cell fitted with a YM-1 membrane (1000 MWCO), and tested for growth potentiating activity by tibial line bioassay (Table 5).

TABLE 5

| | STEP I FRACTIONS: | | | | |
|---|---|---|---|---|---|
| SAMPLE | PROTEIN mG | TIBIAL WIDTH (μM) | BIOAC- TIVITY TYPE | hGH μG | μG hGH/mg PROTEIN |
| ASSAY #1 | | | | | BATCH A |
| CON- TROL | — | 157 | — | — | — |
| HPMQ-3* | ND | 191 | TYPE I | 11.84 | ND |
| HPMQ-4* | ND | 203 | TYPE I | 15.33 | ND |
| HPMQ-5* | ND | 174 | TYPE II | 8.11 | ND |
| ASSAY #2 | | | | | BATCH B |
| CON- TROL | — | 135 | — | — | — |
| HPMQ-3** | 2.91 | 172 | TYPE I | 7.0 | 2.4 |
| HPMQ-4** | 0.36 | 150 | TYPE II | 3.6 | 10.0 |
| HPMQ-5** | 0.40 | 165 | TYPE I | 5.8 | 14.5 | n = 2–3 rats/group
*HPLC pooled fraction (not concentrated and lyophilized)
**HPLC pooled fraction, concentrated and lyophilized
ND - not determined Active fractions from 4–5 runs were pooled, concentrated on an Amicon-cell fitted with a YM-1 membrane, dialyzed against 0.001M ammonium bicarbonate buffer, and lyophilized.

HPLC-Step 2

Figure 18A:
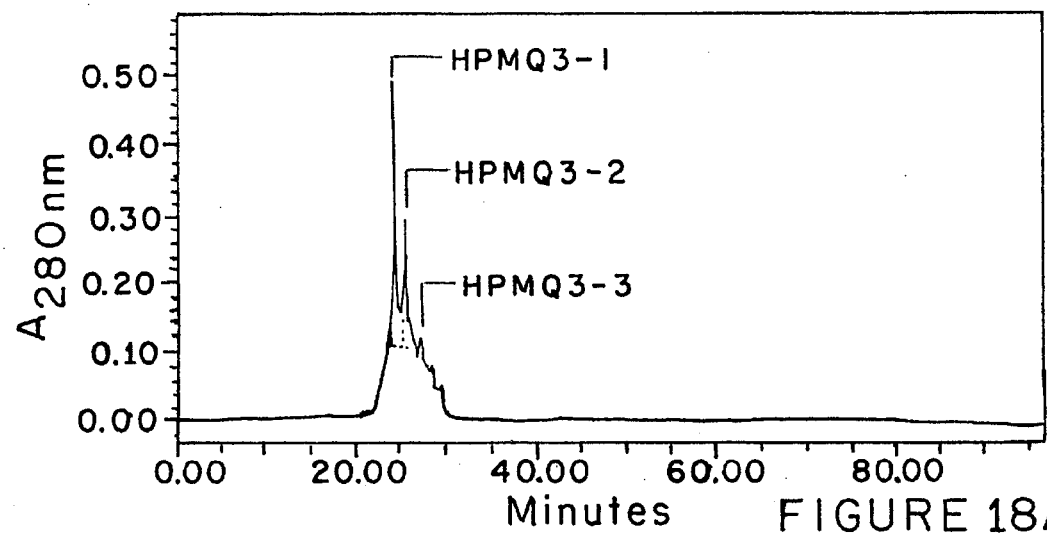
FIGS. 18A, 18B, and 18C are re-chromatography elution profiles of HPLC-Step II fractions HPMQ-3, HPMQ-4 and HPMQ-5, respectively.
Figure 18B:
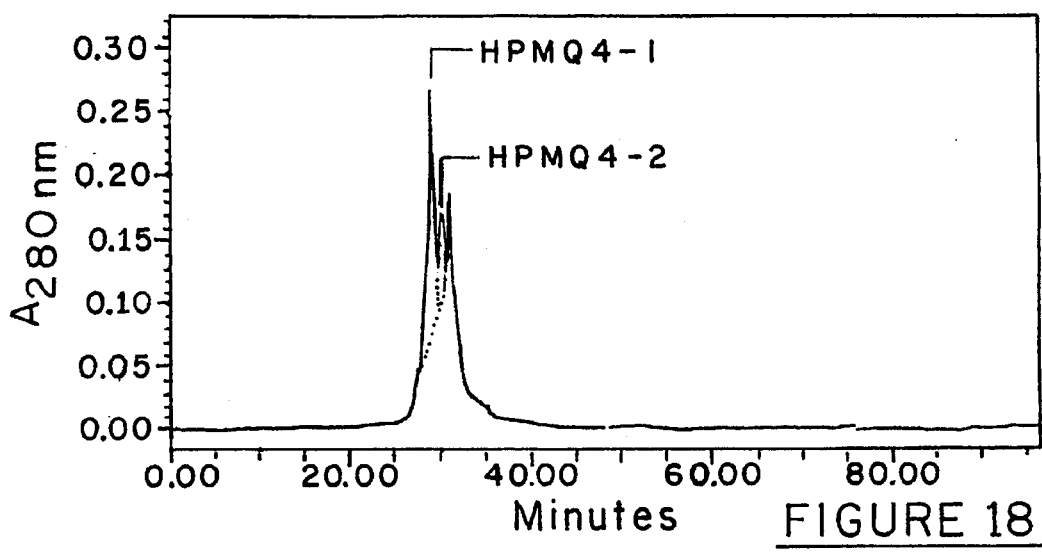
Figure 18C:
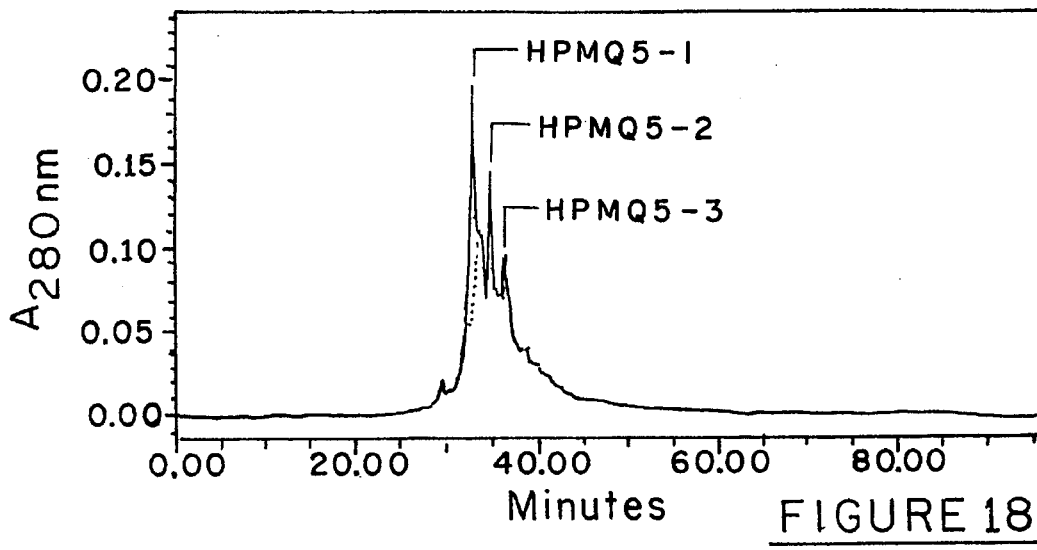

The pooled, lyophilized, bioactive peptide fractions HPMQ-3, HPMQ-4 and HPMQ-5 from step 1 that contained the tibial line bioactivity were reconstituted in 20 mM Tris-HCl, pH 8.0. These fractions were further purified by re-chromatography on the Mono Q column equilibrated with 20 mM Tris-HCl, pH 8.0 (FIGS. 18A, 18B, 18C). The column was eluted with 10 ml of the 20 mM Tris-HCl, pH 8.0, and developed at a flow rate of 1 ml/min with a 30 minute linear gradient from zero to 50% 20 mM Tris-HCl, pH 8.0 containing 0.3M sodium chloride, followed by a 40 min shallow gradient from 50% to 60% Buffer containing 0.36M NaCl, then 60% to 100% Buffer containing 0.6M sodium chloride in 10 minutes, and followed by a 12 min re-equilibration before the next run. The fractions obtained by re-chromatography of fraction HPMQ-3 (FIG. 18A) were pooled as follows: HPMQ3-1 (fr. 24–26), HPMQ3-2 (fr. 27), HPMQ3-3 (fr. 28–34). Similarly, the fractions obtained by re-chromatography of HPMQ-4 (FIG. 18B) and HPMQ-5 (FIG. 18C) were pooled as HPMQ4-1 (fr. 27–29 ) and HPMQ4-2 (fr. 30–33) and HPMQ5-1 (fr. 32–34), HPMQ5-2 (fr. 35) and HPMQ5-3 (fr. 36–38), respectively. The fractions were concentrated and dialyzed on an Amicon cell fitted with a YM-1 membrane (1000 MWCO), lyophilized, and tested for growth potentiating activity in tibial line bioassay (Table 6).

TABLE 6

STEP II FRACTIONS:

| SAMPLE | PROTEIN mG | TIBIAL WIDTH (μM) | BIOAC-TIVITY TYPE | hGH μG | μG hGH/mg PROTEIN |
|---|---|---|---|---|---|
| CONTROL | — | 149 | — | — | — |
| HPMQ3-1 | 0.38 | 138 | — | 0.0 | 0.0 |
| HPMQ3-2 | 0.54 | 152 | — | 0.0 | 0.0 |
| HPMQ3-3 | 0.59 | 165 | TYPE II | 5.71 | 9.6 |
| HPMQ4-1 | 0.11 | 173 | TYPE II | 7.37 | 67.0 |
| HPMQ4-2 | 0.47 | 171 | TYPE II | 6.91 | 15.0 |
| HPMQ5-1 | 0.06 | 158 | TYPE II | 4.52 | 75.0 |
| HPMQ5-2 | 0.02 | 176 | TYPE I | 8.09 | 404.0 |
| HPMQ5-3 | 0.11 | 162 | TYPE II | 5.23 | 47.0 | n = 2 rats/group

The increased purity of active peptides is reflected by their increased specific activity between steps 1 and steps 2 (Table 7).

TABLE 7

| HPLC - STEP 1 | | HPLC - STEP II | | FOLD INCREASE |
|---|---|---|---|---|
| FRACTION | μg hGH/mg PROTEIN | FRACTION | μG hGH/mg PROTEIN | IN TIBIAL ACTIVITY |
| HPMQ-3 | 2.4 | HPMQ3-3 | 9.6 | 4.0 |
| HPMQ-4 | 10.0 | HPMQ4-1 | 67.0 | 6.7 |
|  |  | HPMQ4-2 | 15.0 | 1.5 |
| HPMQ-5 | 14.5 | HPMQ5-1 | 75.0 | 5.2 |
|  |  | HPMQ5-2 | 404.0 | 27.8 |
|  |  | HPMQ5-3 | 47.0 | 3.2 |

HPLC-Step 3

The pooled, lyophilized bioactive peptide fractions HPMQ3-3, HPMQ4-1, HPMQ4-2, HPMQ5-1, HPMQ5-2 and HPMQ5-3 that contained the tibial line activity were reconstituted in 0.05M sodium phosphate/sodium sulphate buffer, pH 7.5. These peptide fractions were separately purified by application on a Shodex sizing column (8mm× 300mm, Waters, Milford, Mass.). The column was equilibrated and eluted with 0.05M sodium phosphate/sodium sulphate buffer, pH 7.5. The peptide fractions were pooled as indicated (FIG. 19 and 20). Pooled fractions were concentrated, dialysed, lyophilized and tested for growth potentiating activity in tibial line assay (Table 8).

TABLE 8

STEP III FRACTIONS:

| SAMPLE | | PROTEIN μg | TIBIAL WIDTH (μM) | BIOAC-TIVITY TYPE | hGH μG |
|---|---|---|---|---|---|
| CONTROL | | — | 177 | — | — |
| MQ3-3-1 | (HPL-1) | ND | 214 | TYPE-I | 16.10 |
| MQ3-3-2 |  | 1.03 | 173 |  | 0.0 |
| MQ3-3-3 |  | 1.94 | 177 |  | 0.0 |
| MQ3-3-4 | (HPL-2) | 1.26 | 194 | TYPE-II | 8.96 |
| MQ4-2-1 |  | 5.01 | 163 |  | 0.0 |
| MQ4-2-2 | (HPL-4) | 7.06 | 188 | TYPE-II | 7.76 |
| MQ4-2-3 |  | ND | 161 |  | 0.0 |
| MQ4-2-4 |  | ND | 175 |  | 0.0 |
| CONTROL | | — | 167 | — | — |
| MQ4-1-1 | (HPL-3) | ND | 201 | TYPE-I | 11.10 |
| CONTROL | | — | 167 | — | — |
| MQ5-1-1 |  | ND | 157 |  | 0.0 |
| MQ5-1-2 | (HPL-5) | ND | 187 | TYPE-II | 7.44 |
| MQ5-1-3 | (HPL-6) | ND | 178 | TYPE-II | 5.65 |
| MQ5-1-4 | (HPL-7) | ND | 197 | TYPE-I | 10.01 |
| CONTROL | | — | 167 | — | — |
| MQ5-2-1 | (HPL-8) | ND | 171 | TYPE-II | 4.65 |
| CONTROL | | — | 167 | — | — |
| MQ5-3-1 | (HPL-9) | ND | 179 | TYPE-II | 5.82 |
| MQ5-3-2 |  | ND | 162 |  | 0.0 |
| MQ5-3-3 |  | ND | 153 |  | 0.0 |
| MQ5-3-4 |  | ND | 164 |  | 0.0 |
| CONTROL | | — | 177 | — | — |
| MQ4-1-2 |  | ND | 167 |  | 0.0 |
| MQ4-1-3 |  | ND | 170 |  | 0.0 |
| MQ4-1-4 |  | ND | 165 |  | 0.0 |
| MQ5-2-2 |  | ND | 163 |  | 0.0 |
| MQ5-2-3 |  | ND | 160 |  | 0.0 |
| MQ5-2-4 |  | ND | 160 |  | 0.0 | n = 1 or 2 rats/group
ND = Not detectable because the protein concentration of the fractions were below the sensitivity (1 μg) of the protein assay standard (Lowry et al., 1951).

Protein Determination

The protein content of the purified peptide was determined by the method of (Lowry, O. H., et al. 1951. *J. Biol. Chem.* 193:265–274) with bovine serum albumin as the standard.

Tibial Growth Bioassay

The tibial line bioassay was performed according to the procedure described in Example 1.

Results

Figure 16:
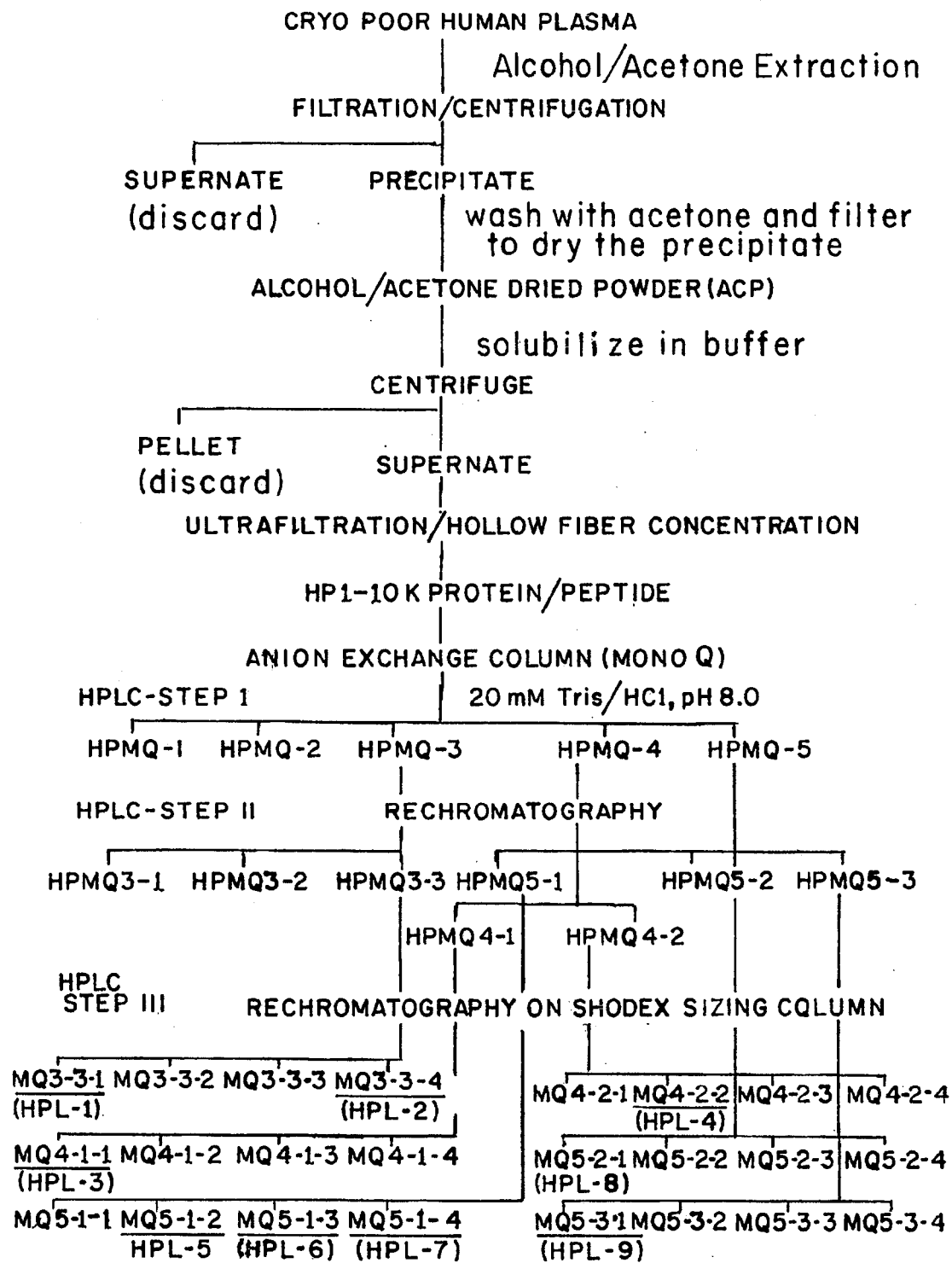
FIG. 16 is a schematic outline which summarizes the procedure used for the purification of the TGPP from human plasma.

FIG. 16 outlines the procedure used for the purification of growth potentiating peptides from human plasma.

FIGS. 17A and 17B depict the chromatographic elution profiles of human plasma 1–10K protein/peptide obtained from two batches (Batches A and B, respectively) of human plasma. This step yielded 5 fractions. Very low tibial growth activity was detected in fractions HPMQ-1 and HPMQ-2 (not shown in Table 4). Major tibial growth potentiating activity was observed in fraction HPMQ-3, HPMQ-4 and HPMQ-5, respectively, (Table 4), eluting at 0.24–0.3M, 0.31–0.37M and 0.36–0.45M NaCl in 20 mM Tris-HCl, pH 8.0, respectively.

The biopotency of the fractions in terms of the concentration of hGH/mg protein was higher by 4- and 6-fold in fraction HPMQ-4 and HPMQ-5, respectively, compared to fraction HPMQ-3.

The bioactive tibial growth potentiating fractions HPMQ-3, HPMQ-4 and HPMQ-5 obtained from HPLC-Step I were further purified by re-chromatography on the Mono Q column using a shallow gradient (HPLC-Step II) developed with NaCl in Tris-HCl buffer, pH 8.0. Re-chromatography of fraction HPMQ-3 yielded three fractions HPMQ3-1, HPMQ3-2 and HPMQ3-3 (FIG. 18A). Fraction HPMQ3-1 and HPMQ3-2 had no activity in tibial line assay whereas fraction HPMQ3-3 showed a 4-fold increase in the tibial growth activity, eluting at 0.3M NaCl with a retention time of 27.483 minutes (Tables 5 and 6). Table 5 shows results of tibial line assay of HPLC Step II re-chromatography fractions of HPMQ-3, HPMQ-4 and HPMQ-5 runs and Table 6 compares the specific activity of tibial growth potentiating peptides after HPLC Step I and Step II runs.

Re-chromatography of the bioactive fraction HPMQ-4 on the Mono Q column yielded two major bioactive tibial growth potentiating fractions HPMQ4-1 and HPMQ4-2 (FIG. 18B), eluting at 0.3–0.306M NaCl with a retention time of 29.117 and 30.35 minutes, respectively. This step resulted in a further 6.7 and 1.5-fold increase in tibial growth potentiating activity respectively (Tables 5 and 6). The biopotency of the peptide fraction HPMQ4-1 and HPMQ4-2 were 67 mg and 15 mg of hGH/mg protein. Based on their retention time and elution concentration of NaCl, it appears that HPMQ4-1 and HPMQ4-2 tibial growth potentiating peptides may be similar to the tibial growth potentiating peptides found in human pituitaries (Example 1).

Re-chromatography of fraction HPMQ-5 yielded three fractions HPMQ5-1, HPMQ5-2 and HPMQ5-3 (FIG. 18C), eluting at 0.303–0.306M concentration of NaCl. Major tibial growth potentiating activity was found in fraction HPMQ5-2 (Tables 5 and 6), eluting at 0.304M NaCl with a retention time of 35.2 minutes. This step resulted in a further 27.8 fold increase in the tibial growth potentiating activity. Biopotency of this peptide fraction was 404 mg of hGH/mg protein. Fraction HPMQ5-1 and HPMQ5-3 showed a 5.2- and 3.2-fold increase in the tibial growth activity, with a potency of 75 mg and 47 mg of hGH/mg protein, respectively.

Figure 19A:
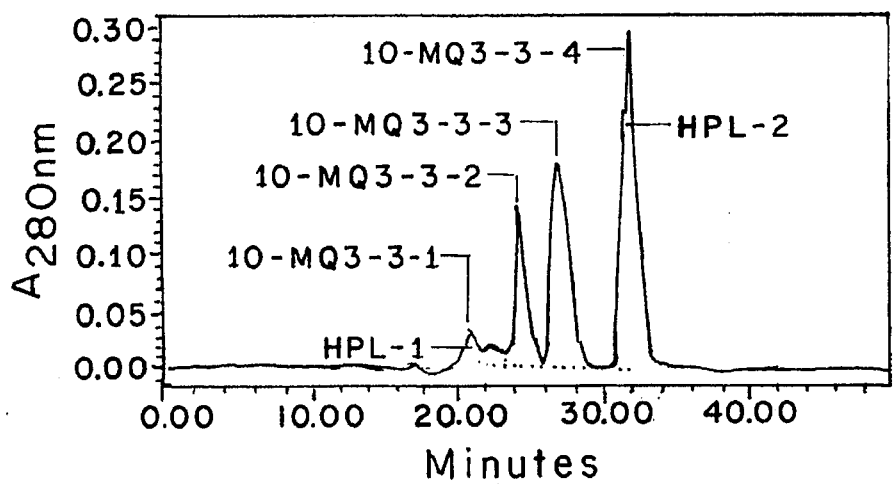
FIGS. 19A, 19B, 19C, 19D, 19E, and 19F show the chromatographic elution profile of step II fractions HPMQ3-3, HPMQ4-1, HPMQ4-2, HPMQ5-1, HPMQ5-2, and HPMQ5-3, respectively, on a Shodex sizing column.
Figure 19B:
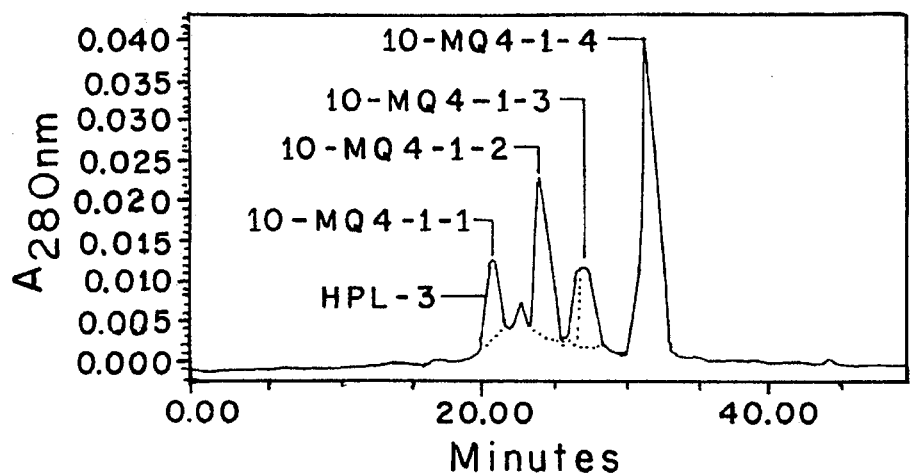
Figure 19C:
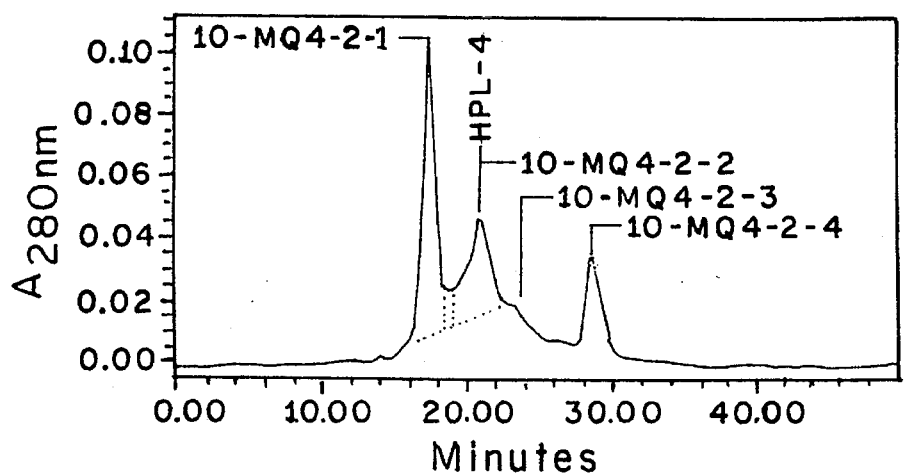
Figure 19D:
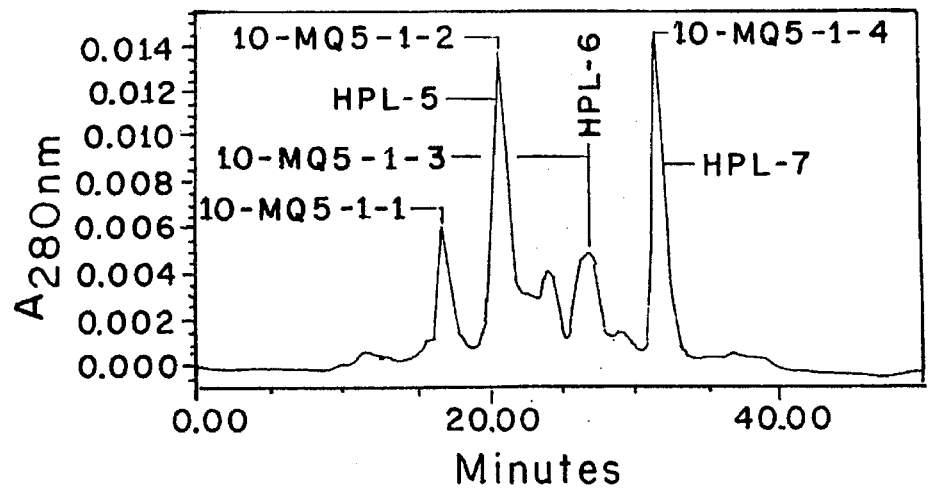
Figure 19E:
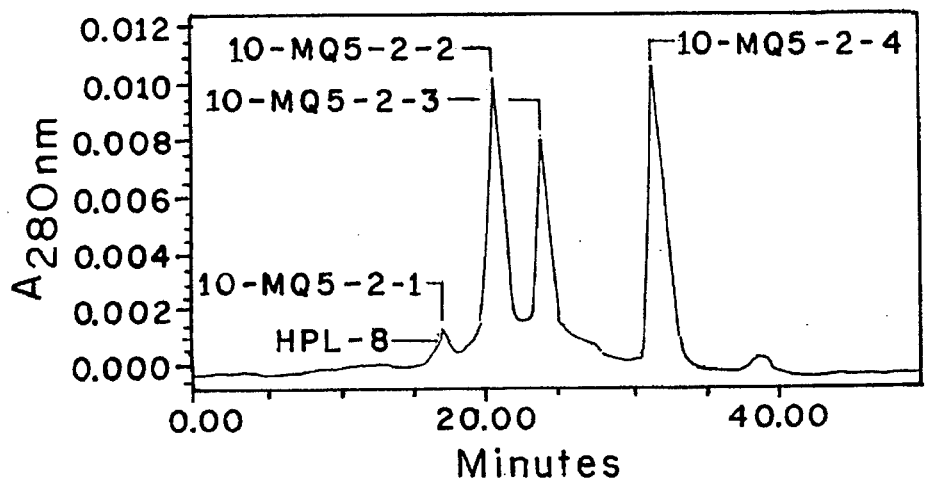
Figure 19F:
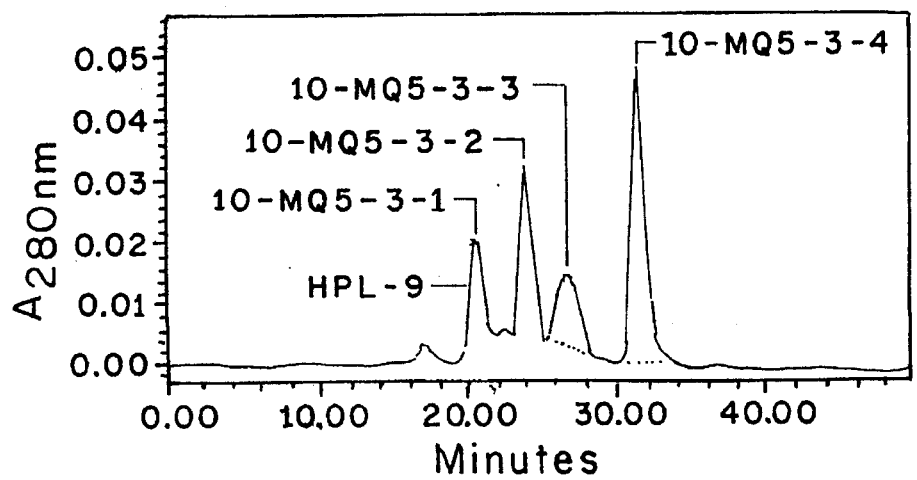
Figure 20A:
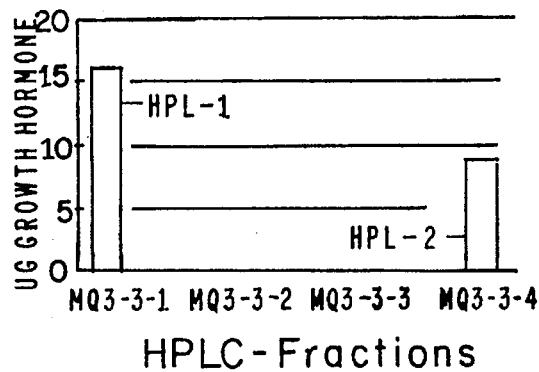
FIGS. 20A, 20B, 20C, 20D, 20E, and 20F show the growth potentiating activity of step II fractions HPMQ3-3, HPMQ4-1, HPMQ4-2, HPMQ5-1, HPMQ5-2 and HPMQ5-3, respectively, on a Shodex sizing column.
Figure 20D:
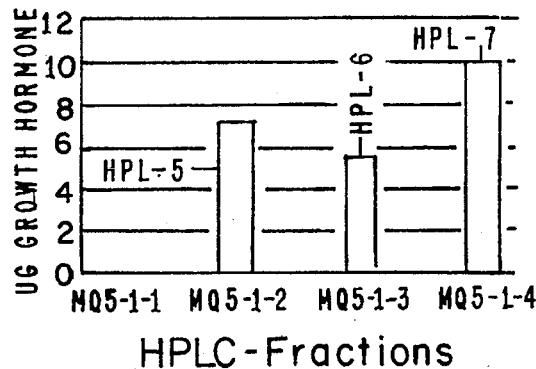
Figure 20B:
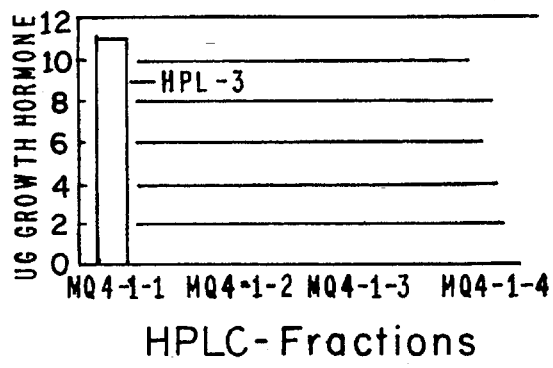
Figure 20E:
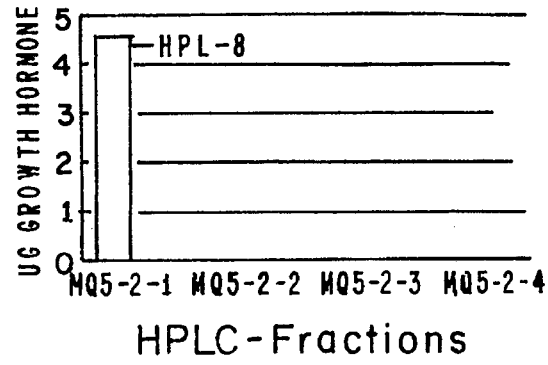
Figure 20C:
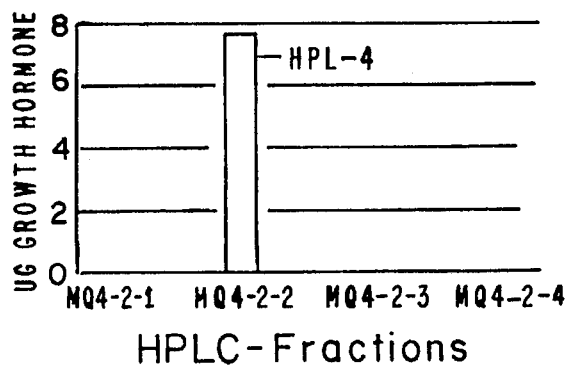
Figure 20F:
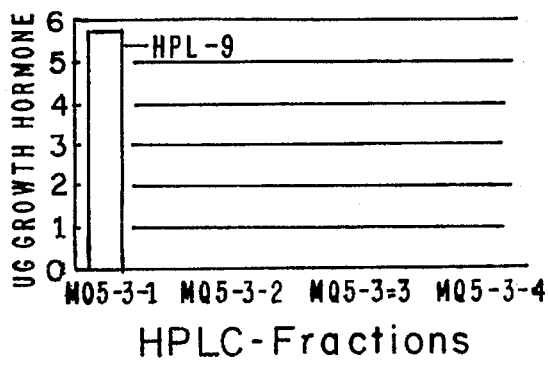

Chromatography of the bioactive growth peptide fractions HPMQ3-3 on a Shodex sizing column yielded 4 fractions (FIG. 19A). Significant growth potentiating activity (TYPE I Bioactivity) was found in peptide fraction MQ3-3-1 (HPL-1) and low tibial line activity (TYPE II Bioactivity) was observed in fraction MQ3-3-4 (HPL-2)(Table 7). Similarly, application of the peptide fraction HPMQ4-1 on the sizing column yielded fractions, (FIG. 19B). Significant TYPE I tibial activity was observed in MQ4-1-1 and this peptide is designated as HPL-3 (Table 7). Application of the fraction HPMQ4-2 on the same column yielded four fractions (FIG. 19C) and the tibial line activity was localized (Table 7) to only one peptide fraction MQ4-2-2 (HPL-4). Chromatography of the peptide fraction HPMQ5-1 on the Shodex column also yielded 4 fractions. Low growth potentiating activity (TYPE II Bioactivity) was located in two fractions MQ5-1-2 and MQ5-1-3 (Table 7) and these peptides were designated as HPL-5 and HPL-6, (FIG. 20A) respectively, while significant growth potentiating activity (TYPE I Bioactivity) was found in fraction MQ5-1-4, designated as HPL-7 (FIG. 20A). Similar application of the remaining peptides HPMQ5-2 and HPMQ5-3 on the Shodex column yielded 4 fractions (FIG. 20B, and 20C). Low tibial potentiating activity (Table 7) (TYPE II Bioactivity) was found in fraction MQ5-2-1 (HPL-8) (FIG. 20B) and MQ5-3-1,(HPL-9) (FIG. 20C), respectively.

What is claimed is:

1. A purified human tibial growth potentiating peptide which has the following characteristics:
   potentiates tibial plate width growth when administered to hypophysectomized rats;
   a molecular weight of less than 10,000 daltons; and
   is unreactive in an enzyme immunoassay for human growth hormone.

2. The purified tibial growth potentiating peptide of claim 1 which is isolated from human pituitary glands.

3. A purified tibial growth potentiating peptide which has the following characteristics:
   potentiates tibial plate width growth when administered to hypophysectomized rats;
   has a molecular weight of 3374–4314;
   an isoelectric point of about 5.1;
   is isolated from human pituitary glands; and
   is unreactive in an enzyme immunoassay for human growth hormone.

4. A purified tibial growth potentiating peptide which has the following characteristics:
   potentiates tibial plate width growth when administered to hypophysectomized rats;
   a molecular weight of less than 10,000 daltons; and
   is unreactive in an enzyme immunoassay for human growth hormone, wherein said peptide has a partial amino acid sequence (SEQ. ID. NO. 2).

5. The purified tibial growth potentiating peptide of claim 1, which is isolated from human plasma.

6. A pharmaceutical composition, comprising:
   an effective amount of human tibial growth potentiating peptide which has the following characteristics:
   potentiates tibial plate width growth in hypophysectomized rats;
   a molecular weight of less than 10,000 daltons;
   is unreactive in an enzyme immunoassay for human growth hormone; and
   a pharmaceutically acceptable carrier therefor.

7. The tibial growth potentiating peptide of claim 1, which has a molecular weight of about 8646.

8. The tibial growth potentiating peptide of claim 1, which has a molecular weight of about 4306.

9. A pharmaceutical composition, comprising:
   an effective amount of tibial growth potentiating peptide which has the following characteristics: potentiates tibial plate width growth when administered to hypophysectomized rats; a molecular weight of less than 10,000 daltons; is unreactive in an enzyme immunoassay for human growth hormone; and has a partial amino acid sequence (SEQ. ID. NO. 2); and
   a pharmaceutically acceptable carrier therefor.

10. A method for stimulating tissue growth which comprises the steps of:
    administering to a patient an effective tissue growth stimulating amount of the composition of claim 6.

11. A method for stimulating tissue growth which comprises the steps of:
    administering to a patient an effective tissue growth stimulating amount of the composition of claim 9.

12. The method of claim 10, wherein said tissue is bone.

13. The method of claim 11, wherein said tissue is bone.

14. The purified tibial growth potentiating peptide of claim 1, which is a mixture of peptides having said characteristics.

15. The purified tibial growth potentiating peptide of claim 1, which has a molecular weight of less than 5,000 daltons.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 25 amino acids
( B ) TYPE: amino acid
( D ) TOPOLOGY: linear ( i i ) MOLECULE TYPE: peptide ( v ) FRAGMENT TYPE: N-terminal ( i x ) FEATURE:
( A ) NAME/KEY: Peptide
( B ) LOCATION: 1..25
( D ) OTHER INFORMATION: /label=peptide
/ note="Amino terminal sequence of HA-1/HA-2
fractions. First 8 residues have heterogeneous
assignments, see Table 4 of Specification."

( i x ) FEATURE:
( A ) NAME/KEY: Modified residue
( B ) LOCATION: 1
( D ) OTHER INFORMATION: /label=amino_terminus
/ note="residue apparently blocked to Edman
degradation."

( i x ) FEATURE:
( A ) NAME/KEY: Ambiguous residue

```
            ( B ) LOCATION: 2
            ( D ) OTHER INFORMATION: /label=amino_proximal
                    / note="proline assignment is ambiguous."

( i x ) FEATURE:
            ( A ) NAME/KEY: Ambiguous residue
            ( B ) LOCATION: 4
            ( D ) OTHER INFORMATION: /label=ambiguous
                    / note="proline assignment is ambiguous."

( i x ) FEATURE:
            ( A ) NAME/KEY: Heterogeneous residue
            ( B ) LOCATION: 6
            ( D ) OTHER INFORMATION: /label=heterogeneous
                    / note="proline predominant residue detected,
                    leucine also seen."

( i x ) FEATURE:
            ( A ) NAME/KEY: Heterogeneous residue
            ( B ) LOCATION: 7
            ( D ) OTHER INFORMATION: /label=heterogeneous
                    / note="serine and leucine observed in about equal
                    amounts"

( i x ) FEATURE:
            ( A ) NAME/KEY: Heterogeneous reside
            ( B ) LOCATION: 8
            ( D ) OTHER INFORMATION: /label=heterogeneous
                    / note="proline predominant; tryptophan, valine,
                    and leucine observed at substantially lower
                    yields."

( x i ) SEQUENCE DESCRIPTION: SEQ ID NO:1:

Xaa  Pro  Gln  Pro  Asn  Pro  Ser  Pro  Ala  Ser  Pro  Val  Val  Val  Gly  Gly
    1                   5                        10                       15

Gly  Ala  Ser  Leu  Pro  Glu  Phe  Xaa  Tyr
                   20                   25

( 2 ) INFORMATION FOR SEQ ID NO:2:

( i ) SEQUENCE CHARACTERISTICS:
            ( A ) LENGTH: 17 amino acids
            ( B ) TYPE: amino acid
            ( D ) TOPOLOGY: linear ( i i ) MOLECULE TYPE: peptide ( v ) FRAGMENT TYPE: internal ( i x ) FEATURE:
            ( A ) NAME/KEY: Peptide
            ( B ) LOCATION: 1..17
            ( D ) OTHER INFORMATION: /label=peptide
                    / note="Represents the homogeneous residues 9-25
                    of tibial growth promoting peptide, see Table 4 of
                    the Specification. "

( x i ) SEQUENCE DESCRIPTION: SEQ ID NO:2:

Ala  Ser  Pro  Val  Val  Val  Gly  Gly  Gly  Ala  Ser  Leu  Pro  Glu  Phe  Xaa
    1                   5                        10                       15

Tyr
```